United States Patent [19]

Behrens et al.

[11] Patent Number: 5,124,378

[45] Date of Patent: * Jun. 23, 1992

[54] STABILIZATION OF AMBIENT CURED COATINGS

[75] Inventors: Rudolf A. Behrens, New Fairfield; Andrew Mar, Norwalk, both of Conn.

[73] Assignee: Ciba-Geigy Corporation, Ardsley, N.Y.

[*] Notice: The portion of the term of this patent subsequent to May 12, 2009 has been disclaimed.

[21] Appl. No.: 259,945

[22] Filed: Oct. 19, 1988

Related U.S. Application Data

[63] Continuation-in-part of Ser. No. 99,420, Sep. 21, 1987, abandoned.

[51] Int. Cl.$^5$ ............................................. C08K 5/34
[52] U.S. Cl. ............................. 524/95; 524/99; 524/100; 524/101; 524/102; 524/103; 544/198; 544/351; 544/383; 544/384; 546/19; 546/20; 546/186; 546/188; 546/189; 546/245
[58] Field of Search .............. 524/95, 99, 100, 101, 524/102, 103; 544/198, 351, 383, 384; 546/19, 20, 186, 188, 189, 245

[56] References Cited

U.S. PATENT DOCUMENTS

| | | | |
|---|---|---|---|
| 4,148,784 | 4/1979 | Malherbe et al. | 524/102 |
| 4,314,933 | 2/1982 | Berner | 524/102 |
| 4,344,876 | 8/1982 | Berner | 524/91 |
| 4,426,471 | 1/1984 | Berner | 524/102 |
| 4,472,547 | 9/1984 | Malherbe | 524/98 |
| 4,547,537 | 10/1985 | Malherbe et al. | 524/97 |
| 4,605,743 | 8/1986 | Malz, Jr. et al. | 546/186 |
| 4,607,104 | 8/1986 | Malz, Jr. et al. | 546/186 |
| 4,691,015 | 9/1987 | Behrens et al. | 524/102 |
| 4,774,275 | 9/1988 | Hisano et al. | 524/370 |

FOREIGN PATENT DOCUMENTS 1196444 11/1985 Canada ............................... 524/102

OTHER PUBLICATIONS

Shlyapintokh et al, "Developments in Polymer Stabilisation", V, 41-70 (1982).
Polymer Chem. Ed. vol. 22, (1984) Journal of Polymer Science.
Chem. Abst. 100, 52579y.
Derwent Abst. 86-199749/31.

Primary Examiner—Kriellion S. Morgan
Attorney, Agent, or Firm—Luther A. R. Hall; Harry Falber

[57] ABSTRACT

N—OR$_1$ substituted hindered amine light stabilizers impart outstanding stabilization properties to ambient cured coatings based on a variety of resins, the stabilized coatings exhibiting improved durability, weatherability, and the like.

28 Claims, No Drawings

STABILIZATION OF AMBIENT CURED COATINGS

BACKGROUND OF THE INVENTION

The instant invention relates to the stabilization of a wide variety of ambient cured coating compositions by the incorporation therein of N- $OR_1$-substituted hindered amine light stabilizers.

Hindered amine light stabilizers are well known to be effective in stabilizing a host of organic substrates including polymers against the deleterious effects of oxygen and light. Such hindered amine light stabilizers have been used in the stabilization of hot-crosslinkable alkyd or acrylic metallic stoving lacquers (U.S. Pat. No. 4,426,472) and in stabilizing acid-catalyzed stoving lacquers based on hot-crosslinkable acrylic polyester or alkyd resins (U.S. Pat. Nos. 4,344,876 and 4,426,471). The hindered amine light stabilizers of these patents do not possess structures having an O-substituted hydroxyl group substituted directly on the hindered N-atom of the compound.

Related hindered amine stabilizers have been utilized individually and in combination with ultra-violet light absorbers to improve the performance characteristics of ambient cured coating systems. Notwithstanding such improvements, there still exists a need to further retard the photooxidation and photodegradation of such ambient cured systems and thereby provide increased effectiveness by maintaining the physical integrity of the coatings. Such effectiveness can be manifested by prevention of embrittlement, cracking, corrosion, erosion, loss of gloss, chalking and yellowing of the coating.

It has now been determined that the aforementioned improvements can be achieved by substitution on the hindered N-atom of the hindered amines with $OR_1$ groups and the utilization of such derivatives in ambient cured coating systems. In particular, the physical integrity of the coatings is maintained to a higher degree with significant reduction in loss of gloss and yellowing. Accordingly, the present invention relates to the use of N—$OR_1$-substituted 2,2,6,6-tetraalkylpiperidine compounds, optionally together with further stabilizers, for stabilizing ambient cured coatings based on alkyd resins; thermoplastic acrylic resins; acrylic alkyds; acrylic alkyd or polyester resins optionally modified with silicon, isocyanates, isocyanurates, ketimines or oxazolidines; and epoxide resins crosslinked with carboxylic acids, anhydrides, polyamines or mercaptans; and acrylic and polyester resin systems modified with reactive groups in the backbone thereof and crosslinked with epoxides; against the degradative effects of light, moisture and oxygen.

The N—$OR_1$- substituted hindered amine compounds of this invention contain the group

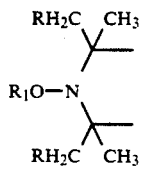

wherein R is hydrogen or methyl, and $R_1$ is $C_1$-$C_{18}$ alkyl, $C_2$-$C_{18}$ alkenyl, $C_2$-$C_{18}$ alkynyl, $C_5$-$C_7$ cycloalkyl, $C_6$-$C_{10}$ bicycloalkyl, $C_5$-$C_8$ cycloalkenyl, $C_6$-$C_{10}$ aryl, $C_7$-$C_9$ aralkyl, $C_7$-$C_9$ aralkyl substituted by alkyl or aryl, or

wherein D is $C_1$-$C_{18}$ alkyl, $C_1$-$C_{18}$ alkoxy, phenyl, phenyl substituted by hydroxy, alkyl or alkoxy, or amino or amino mono- or disubstituted by alkyl or phenyl. Some are known compounds while others are claimed in copending applications Ser. No. 99,414 and 99,419.

More particularly, the instant invention relates to the use of a derivative having one of formulae A to P

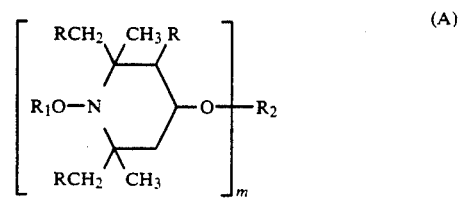
(A)

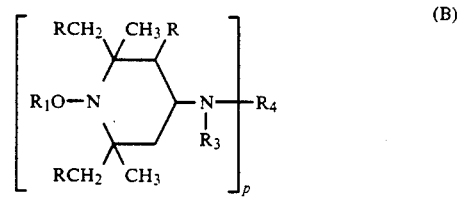
(B)

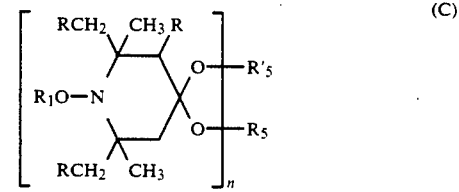
(C)

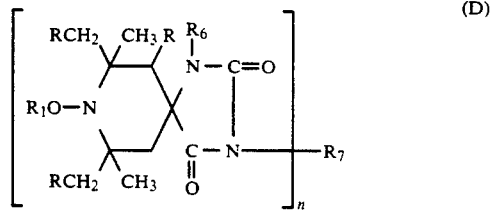
(D)

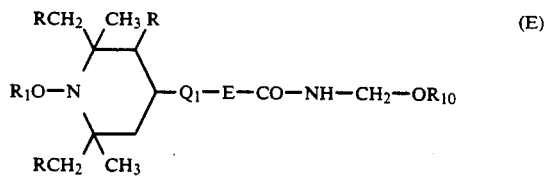
(E)

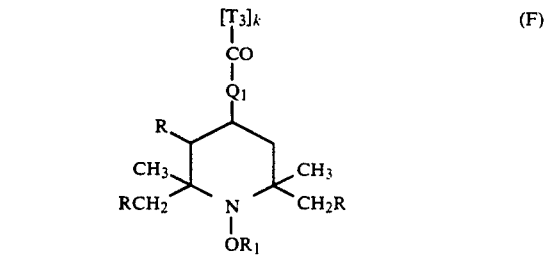
(F)

-continued

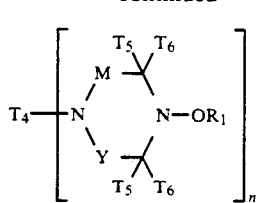 (G)

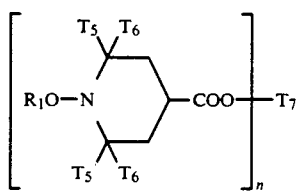 (H)

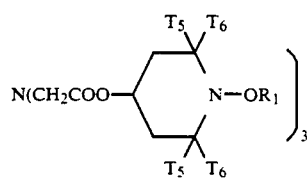 (I)

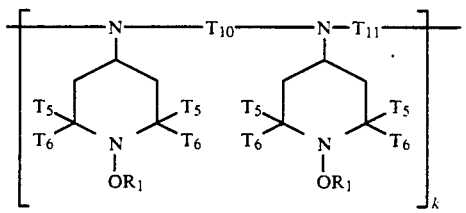 (J)

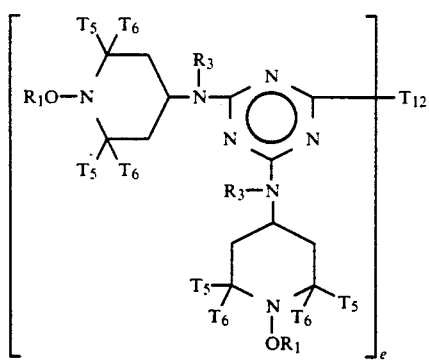 (K)

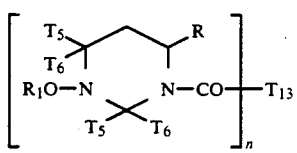 (L)

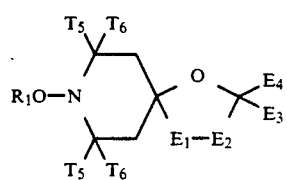

-continued $$\begin{array}{c} R\ CH_3 \quad CH_2R \quad\quad CH_2R\ CH_3\ R \\ R_2O-\!\!\!\!\!\bigcirc\!\!\!\!\!-N-OC-G_1-CO-N-\!\!\!\!\!\bigcirc\!\!\!\!\!-OR_2 \\ CH_3\ CH_2R \quad\quad CH_2R\ CH_3 \end{array}$$ (N)

(O)

(P)

wherein
R is hydrogen or methyl,
$R_1$ is independently $C_1-C_{18}$ alkyl, $C_2-C_{18}$ alkenyl, $C_2-C_{18}$ alkynyl, $C_5-C_{12}$ cycloalkyl, $C_6-C_{10}$ bicycloalkyl, $C_5-C_8$ cycloalkenyl, $C_6-C_{10}$ aryl, $C_7-C_9$ aralkyl, $C_7-C_9$ aralkyl substituted by alkyl or aryl, or $$\begin{array}{c} O \\ \| \\ -C-D \end{array}$$

wherein D is $C_1-C_{18}$ alkyl, $C_1-C_{18}$ alkoxy, phenyl, phenyl substituted by hydroxy, alkyl or alkoxy, or amino or amino mono- or disubstituted by alkyl or phenyl;
m is 1-4,
when m is 1,
$R_2$ is hydrogen, $C_1-C_{18}$ alkyl optionally interrupted by one or more oxygen atoms, $C_2-C_{12}$ alkenyl, $C_6-C_{10}$ aryl, $C_7-C_{18}$ aralkyl, glycidyl, a monovalent acyl radical of an aliphatic, cycloaliphatic, araliphatic or aromatic carboxylic acid, or of a carbamic acid, preferably an acyl radical of an aliphatic carboxylic acid having 2-18 C atoms, of a cycloaliphatic carboxylic acid having 5-12 C atoms or of an aromatic carboxylic acid have 7-15 C atoms, or

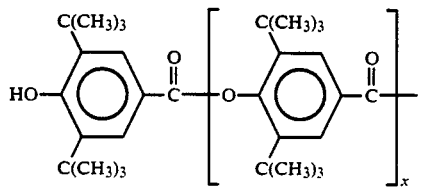 (M)

wherein x is 0 is 1, or

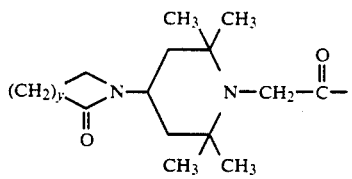

wherein y is 2-4;

when m is 2, $R_2$ is $C_1$-$C_{12}$ alkylene, $C_4$-$C_{12}$ alkenylene, xylylene, a divalent acyl radical of an aliphatic, cycloaliphatic, araliphatic or aromatic dicarboxylic acid or of a dicarbamic acid, preferably an acyl radical of an aliphatic dicarboxylic acid having 2-18 C atoms, of a cycloaliphatic or aromatic dicarboxylic acid having 8-14 C atoms, or of an aliphatic, cycloaliphatic or aromatic dicarbamic acid having 8-14 C atoms;

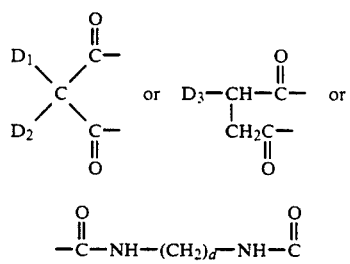

wherein $D_1$ and $D_2$ are independently hydrogen, an alkyl radical containing up to 8 carbon atoms, an aryl or aralkyl radical including 3,5-di-t-butyl-4-hydroxybenzyl radical, $D_3$ is hydrogen, or an alkyl or alkenyl radical containing up to 18 carbon atoms, and d is 0-20;

when m is 3, $R_2$ is a trivalent acyl radical of an aliphatic, unsaturated aliphatic, cycloaliphatic, or aromatic tricarboxylic acid;

when m is 4, $R_2$ is a tetravalent acyl radical of a saturated or unsaturated aliphatic or aromatic tetracarboxylic acid including 1,2,3,4-butanetetracarboxylic acid, 1,2,3,4-but-2-enetetracarboxylic acid, and 1,2,3,5- and 1,2,4,5-pentanetetracarboxylic acid;

is 1, 2 or 3, $R_3$ is hydrogen, $C_1$-$C_{12}$ alkyl, $C_5$-$C_7$ cycloalkyl, $C_7$-$C_9$ aralkyl, $C_2$-$C_{18}$ alkanoyl, $C_3$-$C_5$ alkenoyl or benzoyl;

when p is 1, $R_4$ is hydrogen, $C_1$-$C_{18}$ alkyl, $C_5$-$C_7$ cycloalkyl, $C_2$-$C_8$ alkenyl unsubstituted or substituted by a cyano, carbonyl or carbamide group, aryl, aralkyl, or it is glycidyl, a group of the formula —$CH_2$—$CH(OH)$—Z or of the formula —CO—Z or —CONH—Z wherein Z is hydrogen, methyl or phenyl; or a group of the formulae

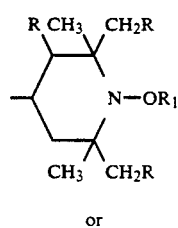

or

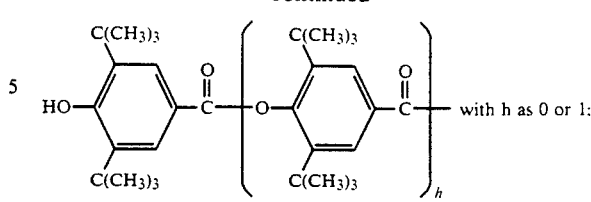 with h as 0 or 1;

or $R_3$ and $R_4$ together when p is 1 can be alkylene of 4 to 6 carbon atoms or 2-oxo-polyalkylene or the cyclic acyl radical of an aliphatic or aromatic 1,2- or 1,3-dicarboxylic acid, when p is 2, $R_4$ is a direct bond or is $C_1$-$C_{12}$ alkylene, $C_6$-$C_{12}$ arylene, xylylene, a —$CH_2CH(OH)$—$CH_2$ group, or a group —$CH_2$—$CH(OH)$—$CH_2$—O—X—O—$CH_2$—$CH(OH)$—$CH_2$— wherein X is $C_2$-$C_{10}$ alkylene, $C_6$-$C_{15}$ arylene or $C_6$-$C_{12}$ cycloalkylene; or, provided that $R_3$ is not alkanoyl, alkenoyl or benzoyl, $R_4$ can also be a divalent acyl radical of an aliphatic, cycloaliphatic or aromatic dicarboxylic acid or dicarbamic acid, or can be the group —CO—; or $R_4$ is

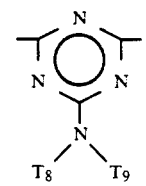

where $T_8$ and $T_9$ are independently hydrogen, alkyl of 1 to 18 carbon atoms, or $T_8$ and $T_9$ together are alkylene of 4 to 6 carbon atoms or 3-oxapentamethylene, preferably $T_8$ and $T_9$ together are 3-oxapentamethylene;

when p is 3, $R_4$ is 2,4,6-triazinyl, n is 1 or 2, when n is 1, $R_5$ and $R'_5$ are independently $C_1$-$C_{12}$ alkyl, $C_2$-$C_{12}$ alkenyl, $C_7$-$C_{12}$ aralkyl, or $R_5$ is also hydrogen, or $R_5$ and $R'_5$ together are $C_2$-$C_8$ alkylene or hydroxyalkylene or $C_4$-$C_{22}$ acyloxyalkylene;

when n is 2, $R_5$ and $R'_5$ together are (—$CH_2$)$_2C(CH_2$—)$_2$;

$R_6$ is hydrogen, $C_1$-$C_{12}$ alkyl, allyl, benzyl, glycidyl or $C_2$-$C_6$ alkoxyalkyl;

when n is 1, $R_7$ is hydrogen, $C_1$-$C_{12}$ alkyl, $C_3$-$C_5$ alkenyl, $C_7$-$C_9$ aralkyl, $C_5$-$C_7$ cycloalkyl, $C_2$-$C_4$ hydroxyalkyl, $C_2$-$C_6$ alkoxyalkyl, $C_6$-$C_{10}$ aryl, glycidyl, a group of the formula —($CH_2$)$_t$—COO—Q or of the formula —($CH_2$)$_t$—O—CO—Q wherein t is 1 or 2, and Q is $C_1$-$C_4$ alkyl or phenyl; or when n is 2, $R_7$ is $C_2$-$C_{12}$ alkylene, $C_6$-$C_{12}$ arylene, a group —$CH_2CH(OH)$—$CH_2$—O—X—O—$CH_2$—$CH(OH)$—$CH_2$— wherein X is $C_2$-$C_{10}$ alkylene, $C_6$-$C_{15}$ arylene or $C_6$-$C_{12}$ cycloalkylene, or a group —$CH_2CH(OCH_2$—$CH(OZ')CH_2$)$_2$— wherein Z' is hydrogen, $C_1$-$C_{18}$ alkyl, allyl, benzyl, $C_2$-$C_{12}$ alkanoyl or benzoyl;

$Q_1$ is —$N(R_8)$— or —O—; E is $C_1$-$C_3$ alkylene, the group —$CH_2$—$CH(R_9)$—O— wherein $R_9$ is hydrogen, methyl or phenyl, the group —($CH_2$)$_3$—NH— or a direct bond;

$R_{10}$ is hydrogen or $C_1$-$C_{18}$ alkyl, $R_8$ is hydrogen, $C_1$-$C_{18}$ alkyl, $C_5$-$C_7$ cycloalkyl, $C_7$-$C_{12}$ aralkyl, cyanoethyl, $C_6$-$C_{10}$ aryl, the group —CH$_2$—CH(R$_9$)—OH wherein $R_9$ has the meaning defined above; a group of the formula

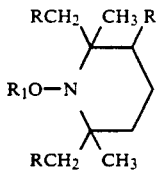

or a group of the formula

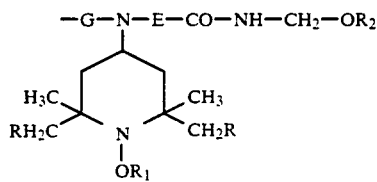

wherein G is $C_2$-$C_6$ alkylene or $C_6$-$C_{12}$ arylene; or $R_8$ is a group —E—CO—NH—CH$_2$—OR$_{10}$;

Formula F denotes a recurring structural unit of a polymer where $T_3$ is ethylene or 1,2-propylene, or is the repeating structural unit derived from an alpha-olefin copolymer with an alkyl acrylate or methacrylate; preferably a copolymer of ethylene and ethyl acrylate, and where k is 2 to 100;

$T_4$ has the same meaning as $R_4$ when p is 1 or 2, $T_5$ is methyl, $T_6$ is methyl or ethyl, or $T_5$ and $T_6$ together are tetramethylene or pentamethylene, preferably $T_5$ and $T_6$ are each methyl, M and Y are independently methylene or carbonyl preferably M is methylene and Y is carbonyl, and $T_4$ is ethylene where n is 2;

$T_7$ is the same as $R_7$, and $T_7$ is preferably octamethylene where n is 2, $T_{10}$ and $T_{11}$ are independently alkylene of 2 to 12 carbon atoms, or $T_{11}$ is

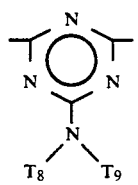

$T_{12}$ is piperazinyl,
—NR$_{11}$—(CH$_2$)$_d$—NR$_{11}$— or

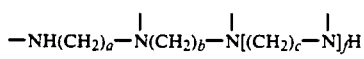

where $R_{11}$ is the same as $R_3$ or is also

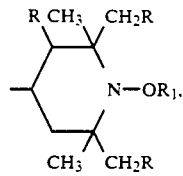

a, b and c are independently 2 or 3, and f is 0 or 1, preferably a and c are each 3, b is 2 and f is 1; and e is 2, 3 or 4, preferably 4;

$T_{13}$ is the same as $R_2$ with the proviso that $T_{13}$ cannot be hydrogen when n is 1;

$E_1$ and $E_2$, being different, each are —CO— or —N-(E$_5$)where $E_5$ is hydrogen, $C_1$-$C_{12}$ alkyl or $C_4$-$C_{22}$ alkoxycarbonylalkyl, preferably $E_1$ is —CO— and $E_3$ is hydrogen, alkyl of 1 to 30 carbon atoms, phenyl, naphthyl, said phenyl or said naphthyl substituted by chlorine or by alkyl of 1 to 4 carbon atoms, or phenylalkyl of 7 to 12 carbon atoms, or said phenylalkyl substituted by alkyl of 1 to 4 carbon atoms, $E_4$ is hydrogen, alkyl of 1 to 30 carbon atoms, phenyl, naphthyl or phenylalkyl of 7 to 12 carbon atoms, or $E_3$ and $E_4$ together are polymethylene of 4 to 17 carbon atoms, or said polymethylene substituted by up to four alkyl groups of 1 to 4 carbon atoms, preferably methyl, $R_2$ of formula (N) is a previously defined when m is 1, $G_1$ is a direct bond, $C_1$-$C_{12}$ alkylene, phenylene or —NH—G'—NH wherein G' is $C_1$-$C_{12}$ alkylene, and $E_6$ is an aliphatic or aromatic tetravalent radical.

In the structures A to P, if any substituents are $C_1$-$C_{18}$ alkyl, they are for example methyl, ethyl, n-propyl, n-butyl, sec-butyl, tert-butyl, n-hexyl, n-octyl, 2-ethylhexyl, n-nonyl, n-decyl, n-undecyl, n-dodecyl, n-tridecyl, n-tetradecyl, n-hexadecyl or n-octadecyl. Typical cycloalkyl groups include cyclopentyl, cyclohexyl and cyclododecyl; typical cycloalkenyl groups include cyclohexenyl; while typical aralkyl groups include benzyl, alpha-methylbenzyl, alpha,alpha-dimethylbenzyl or phenethyl. $C_1$-$C_{12}$ alkyl and cyclohexyl are preferred.

If $R_2$ is a monovalent acyl radical of a carboxylic acid, it is for example an acyl radical of acetic acid, stearic acid, salicylic acid, benzoic acid or β-(3,5-di-tert-butyl-4-hydroxyphenyl) propionic acid.

If $R_2$ is a divalent acyl radical of a dicarboxylic acid, it is for example an acyl radical of oxalic acid, adipic acid, succinic acid, suberic acid, sebacic acid, phthalic acid dibutylmalonic acid, dibenzylmalonic acid or butyl-(3,5-di-tert-butyl-4-hydroxybenzyl)-malonic acid, or bicycloheptenedicarboxylic acid, with succinates, sebacates, phthalates and isophthalates being preferred.

If $R_2$ is a divalent acyl radical of a dicarbamic acid, it is for example an acyl radical of hexamethylenedicarbamic acid or of 2,4-toluylenedicarbamic acid.

The following compounds are examples of polyalkylpiperidine starting materials useful in making the hydroxylamine derivatives of formula A.
4-benzyloxy-2,2,6,6-tetramethylpiperidine
4-acryloyloxy-2,2,6,6-tetramethylpiperidine
4-hydroxy-2,2,6,6-tetramethylpiperidine
4-stearoyloxy-2,2,6,6-tetramethylpiperidine
di-(2,2,6,6-tetramethylpiperidin-4-yl) adipate
di-(2,2,6,6-tetramethylpiperidin-4-yl) sebacate
di-(2,2,6,6-tetramethylpiperidin-4-yl)phthalate
alpha,alpha'-(di-2,2,6,6-tetramethyl piperidine-4-oxy)-p-xylene
di-(2,2,6,6-tetramethylpiperidin-4-yl)succinate
di-(2,2,6,6-tetramethylpiperidin-4-yl)malonate
1,4-dihydroxy-2,2,6,6-tetramethylpiperidine
1-acetoxy-4-hydroxy-2,2,6,6-tetramethylpiperidine
(2,2,6,6-tetramethylpiperidin-4-yl)-[4-(2-oxoazepin-1-yl)-2,2,6,6-tetramethylpiperidin-4-yl]acetate.

As $C_7$–$C_9$ aralkyl, $R_3$ is particularly phenethyl or above all benzyl.

As $C_2$–$C_{18}$ alkanoyl, $R_3$ for example propionyl, butyryl, octanoyl, dodecanoyl, hexadecanoyl, octadecanoyl, but preferably acetyl.

If $R_4$ is $C_2$–$C_8$ alkenyl unsubstituted or substituted by a cyano, carbonyl or carbamide group, it is for example 1-propenyl, allyl, methallyl, 2-butenyl, 2-pentenyl, 2-hexenyl, 2-octenyl, 2,2-dicyanovinyl, 1-methyl-2-cyano-2-methoxycarbonyl-vinyl or 2,2-diacetylaminovinyl.

If any substituents are $C_2$–$C_{12}$ alkylene, they are for example ethylene, propylene, 2,2-dimethylpropylene, tetramethylene, hexamethylene, octamethylene, decamethylene or dodecamethylene.

If any substituents are $C_6$–$C_{15}$ arylene, they are for example o-, m- or p-phenylene, 1,4-naphthylene or 4,4'-diphenylene.

As $C_6$–$C_{12}$ cycloalkylene, X is especially cyclohexylene.

The following compounds are examples of polyalkylpiperidine starting materials useful in making the hydroxylamine derivatives of formula B.
N,N'-bis(2,2,6,6-tetramethylpiperidin-4-yl)-hexamethylene-1,6-diamine,
N,N'-bis-(2,2,6,6-tetramethylpiperidin-4-yl)-hexamethylene-1,6-diacetamide,
4-benzylamino-2,2,6,6-tetramethylpiperidine,
N-n-butyl—N-(2,2,6,6-tetramethylpiperidin-4-yl)-4-hydroxy-3,5-di-tert.butyl benzamide,
N,N'-bis-(2,2,6,6-tetramethylpiperidin-4-yl)—N,N'-dibutyl-adipamide,
N,N'-bis-(2,2,6,6-tetramethylpiperidin-4-yl)—N,N'-dicyclohexyl-(2-hydroxypropylene-diamine),
N,N'-bis-(2,2,6,6-tetramethylpiperidin-4-yl)-p-xylylenediamine,
4-(3-methyl-4-hydroxy-5-tert-butyl-benzoyl acetamido)-2,2,6,6-tetramethylpiperidine,
alpha-cyano-β-methyl-β-[N-(2,2,6,6-tetramethylpiperidin-4-yl]-amino-acrylic acid methyl ester
1-acetoxy—N-butylamino-2,2,6,6-tetramethylpiperidine 1-oxyl-2,2,6,6-tetramethylpiperidin-4-one If $R_5$ is $C_2$–$C_8$ alkylene or hydroxyalkylene, it is for example ethylene, 1-methyl-ethylene, propylene, 2-ethylpropylene or 2-ethyl-2-hydroxymethylpropylene.

As $C_4$–$C_{22}$ acyloxyalkylene, $R_5$ is for example 2-ethyl-2-acetoxymethyl-propylene.

The following compounds are examples for polyalkylpiperidine starting materials useful in making the hydroxylamine derivatives of formula C.
9-aza-8,8,10,10-tetramethyl-1,5-dioxaspiro[5.5]undecane,
9-aza-8,8,10,10-tetramethyl-3-ethyl-1,5-dioxaspiro[5.5]undecane,
2,2,6,6-tetramethylpiperidine-4-spiro-2'-(1',3'-dioxane)-5'-spiro-5''-(1'',3''-dioxane)-2''-spiro-4'''-(2''',2'''-6''',6'''-tetramethylpiperidine).

If any substituents are $C_2$–$C_6$ alkoxyalkyl, they are for example methoxymethyl, ethoxymethyl, propoxymethyl, tert-butoxyethyl, ethoxyethyl, ethoxypropyl, n-butoxyethyl, tert-butoxyethyl, isopropoxyethyl or propoxypropyl.

If $R_7$ is $C_3$–$C_5$ alkenyl, it is for example 1-propenyl, allyl, methallyl, 2-butenyl or 2-pentenyl.

As $C_7$–$C_9$ aralkyl, $R_7$ is in particular phenethyl or above all benzyl; and as $C_5$–$C_7$ cycloalkyl, $R_7$ is especially cyclohexyl.

If $R_7$ is $C_2$–$C_4$ hydroxyalkyl, it is for example 2-hydroxyethyl, 2-hydroxypropyl, 3-hydroxypropyl, 2-hydroxybutyl or 4-hydroxybutyl.

As $C_6$–$C_{10}$ aryl, $R_7$ is in particular phenyl, or alpha- or β-naphthyl which is unsubstituted or substituted by halogen or $C_1$–$C_4$ alkyl.

If $R_7$ is $C_2$–$C_{12}$ alkylene, it is for example ethylene, propylene 2,2-dimethylpropylene, tetramethylene, hexamethylene, octamethylene, decamethylene or dodecamethylene.

If $R_7$ is $C_6$–$C_{12}$ arylene, it is for example o-, m- or p-phenylene, 1,4-naphthylene or 4,4'-diphenylene.

If Z' is $C_2$–$C_{12}$ alkanoyl, it is for example propionyl, butyryl, octanoyl, dodecanoyl or preferably acetyl.

The following compounds are examples of polyalkylpiperidine starting materials useful in making hydroxylamine derivatives of formula D.
3-benzyl-1,3,8-triaza-7,7,9,9-tetramethylspiro[4.5]decane-2,4-dione,
3-n-octyl-1,3,8-triaza-7,7,9,9-tetramethylspiro[4.5]decane-2,4-dione,
3-allyl-1,3,8-triaza-1,7,7,9,9-pentamethylspiro[4.5]decane-2,4-dione,
or the compounds of the following formulae:

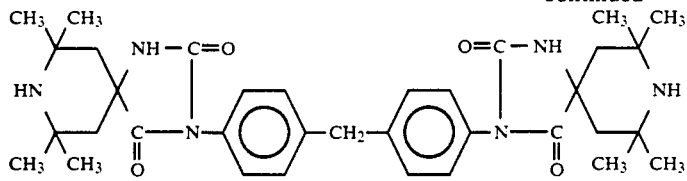 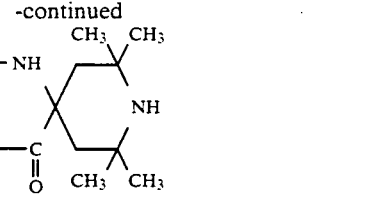

As $C_5$–$C_7$ cycloalkyl, $R_8$ is in particular cyclohexyl.

As $C_6$–$C_{10}$ aryl, $R_8$ is particularly phenyl, or alpha- or β-naphthyl which is unsubstituted or substituted with halogen or $C_1$–$C_4$ alkyl.

As $C_1$–$C_3$ alkylene, E is for example methylene, ethylene or propylene.

As $C_2$–$C_6$ alkylene, G is for example ethylene, propylene, 2,2-dimethylpropylene, tetramethylene or hexamethylene; and as $C_6$–$C_{12}$ arylene, G is o-, m- or p-phenylene, 1,4-naphthylene or 4,4'-diphenylene.

The following compounds are examples of polyalkylpiperidine starting materials useful in making the hydroxylamine derivatives of formula E.

N-hydroxymethyl—N'-2,2,6,6-tetramethylpiperidin-4-yl urea,

N-methoxymethyl—N'-2,2,6,6-tetramethylpiperidin-4-yl urea,

N-methoxymethyl—N'-n-dodecyl—N'-2,2,6,6-tetramethylpiperidin-4-yl-urea, and

O-(2,2,6,6-tetramethylpiperidin-4-yl)—N-methoxymethylurethane.

When the instant hydroxylamine derivative is of formula F, the following polymeric compounds are examples of starting materials useful in preparing said derivatives.

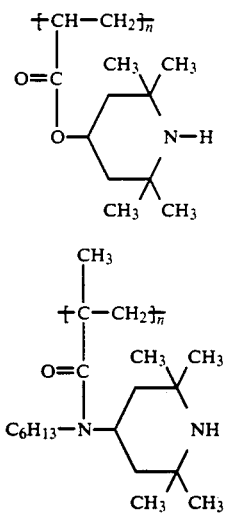

Additional starting hindered amine derivatives include for formula J:

poly-{[6-[(1,1,3,3-tetramethylbutyl)-imino]-1,3,5-triazine-2,4-diyl][2-(1-oxyl-2,2,6,6-tetramethyl piperidyl)-imino]-hexamethylene-4[4-(1-oxyl-2,2,6,6-tetramethylpiperidyl]-imino]}, For compounds of formula O, $R_3$ is preferably $C_1$–$C_{12}$ alkyl and $C_5$–$C_7$ cycloalkyl and more preferably methyl, octyl, dodecyl and cyclohexyl.

For compounds of formula P, the following species are typical of tetracarboxylic acid dianhydrides suitable for the preparation thereof:

2,3,9,10-perylene tetracarboxylic acid dianhydride
1,4,5,8-naphthalene tetracarboxylic acid dianhydride
2,6-dichloronaphthalene-1,4,5,8-tetracarboxylic acid dianhydride
2,7-dichloronaphthalene-1,4,5,8-tetracarboxylic acid dianhydride
2,3,6,7-tetrachloronaphthalene-1,4,5,8-tetracarboxylic acid dianhydride
phenanthrene-1,8,9,10-tetracarboxylic acid dianhydride
2,3,3',4'-benzophenonetetracarboxylic acid dianhydride
pyromellitic dianhydride
3,3',4,4'-benzophenonetetracarboxylic acid dianhydride
2,2',3,3,-benzophenonetetracarboxylic acid dianhydride
3,3',4,4'-biphenyltetracarboxylic acid dianhydride
2,2',3,3'-biphenyltetracarboxylic acid dianhydride
4,4'-isopropylidenediphthalic anhydride
3,3'-isopropylidenediphthalic anhydride
4,4'-oxydiphthalic anhydride
4,4'-sulfonyldiphthalic anhydride
3,3'-oxydiphthalic anhydride
4,4'-methylenediphthalic anhydride
4,4'-thiodiphthalic anhydride
4,4'-ethylidenediphthalic anhydride
2,3,6,7-naphthalenetetracarboxylic acid dianhydride
1,2,4,5-naphthalenetetracarboxylic acid dianhydride
1,2,5,6-naphthalenetetracarboxylic acid dianhydride
benzene-1,2,3,4-tetracarboxylic acid dianhydride
pyrazine-2,3,5,6-tetracarboxylic acid dianhydride.

The following compounds are examples of hydroxylamines derivatives applicable for use in the invention:

1. di-(1-acetoxy-2,2,6,6-tetramethylpiperidin-4-yl)phthalate
2. di-(1-acetoxy-2,2,6,6-tetramethylpiperidin-4-yl)isophthalate
3. di-(1-acetoxy-2,2,6,6-tetramethylpiperidin-4-yl) sebacate
4. di-(1-acetoxy-2,2,6,6-tetramethylpiperidin-4-yl) succinate
5. di-(1-acetoxy-2,2,6,6-tetramethylpiperidin-4-yl) adipate
6. di-(1-acetoxy-2,2,6,6-tetramethylpiperidin-4-yl) n-butylmalonate
7. di-(1-acetoxy-2,2,6,6-tetramethylpiperidin-4-yl) 2,2-diethylmalonate
8. poly-[6-[(1,1,3,3-tetramethylbutyl)-imino]-1,3,5-triazine-2,4-diyl][2-(1-acetoxy-2,2,6,6-tetramethylpiperidyl)-imino]-hexamethylene-[4-(1-acetoxy-2,2,6,6-tetramethylpiperidyl)-imino]
9. 1,4-diacetoxy-2,2,6,6-tetramethylpiperidine
10. 1-acetoxy-4-hydroxy-2,2,6,6-tetramethylpiperidine
11. di-(1-propionoxy-2,2,6,6-tetramethylpiperidin-4-yl)adipate
12. di-(4-benzoyloxy-2,2,6,6-tetramethylpiperidin-4-yl)oxalate
13. (1-acetoxy-2,2,6,6-tetramethylpiperidin-4-yl)-4-hydroxy-3,5-di-tert.butylbenzoate
14. 2-(4-hydroxy-3,5-di-tert.butylbenzyl)-2-(1-acetoxy-2,2,6,6-tetramethylpiperidin-4-yl) n-butylmalonate 15. N-(1-acetoxy-2,2,6,6-tetramethylpiperidin-4-yl)N-(n-butyl)-4-(4-hydroxy-3,5-di-tert.butylbenzoyloxy)-3,5-di-tert.butylbenzamide
16. 1,6-di-(N-acetyl—N-(1-acetoxy-2,2,6,6-tetramethylpiperidin-4-yl)]aminohexane
17. di-(1-acetoxy-2,2,6,6-tetramethylpiperidin-4-yloxy)-hexane-1,6-dicarbamate
18. 1-acetoxy-4-(N-acetyl—N-n-dodecylamino)-2,2,6,6-tetramethylpiperidine
19. di-(1-propionoxy-2,2,6,6-tetramethylpiperidin-4-yl)succinate
20. di-(4-n-octadecanoyloxy-2,2,6,6-tetramethylpiperazin-1-yl)oxalate
21. 1,4-di-(2-ethylhexanoyloxy)-2,2,6,6-tetramethylpiperidine
22. di-(1-benzoyloxy-2,2,6,6-tetramethylpiperidin-4-yl)sebacate
23. 1-benzoyloxy-4-(N-n-butyl—N-benzoylamino)-2,2,6,6-tetramethylpiperidine
24. 1-(1-benzoyloxy-2,2,6,6-tetramethylpiperdin-4-yl)azepin-2-one
25. 1-benzoyloxy-1'-benzyloxy-di-(2,2,6,6-tetramethylpiperidin-4-yl)]isophthalate
26. 1,4-di-(4-hydroxy-3,5-di-tert-butylbenzoyloxy)-2,2,6,6-tetramethylpiperidine
27. n-butyl-(4-benzoyloxy-2,2,6,6-tetramethylpiperidin-4-yl)carbonate
28. 1-carbamoyloxy-4-benzoyloxy-2,2,6,6-tetramethylpiperidine
29. di(1-carbamoyloxy-2,2,6,6-tetramethylpiperidin-4-yl)sebacate
30. di-(1-n-butylcarbamoyloxy-2,2,6,6-tetramethylpiperidin-4-yl)2,2-diethylmalonate
31. di-(4-benzoyloxy-2,2,6,6-tetramethylpiperidin-1-yl)-2,4,4-trimethylhexane-1,6-dicarbamate
32. alpha,alpha'-(di-1-ethoxy-2,2,6,6-tetramethylpiperidin-4-yloxy)-p-xylene
33. 4-benzyloxy-1-ethoxy-2,2,6,6-tetramethylpiperidine
34. 1,4-dibenzyloxy-2,2,6,6-tetramethylpiperidine
35. alpha,alpha'-(di-1-benzyloxy-2,2,6,6-tetramethylpiperidin-4-yloxy)-p-xylene
36. di-(1-benzyloxy-2,2,6,6-tetramethylpiperidin-4-yl)sebacate
37. 4-benzoyloxy-1-(alpha-methylbenzyloxy)-2,2,6,6-tetramethylpiperidine
38. di-[1-(alpha-methylbenzyloxy)-2,2,6,6-tetramethylpiperidin-4-yl]sebacate
39. 1,4-dimethoxy-2,2,6,6-tetramethylpiperidine
40. 4-benzoyloxy-1-methoxy-2,2,6,6-tetramethylpiperidine
41. di-(1-methoxy-2,2,6,6-tetramethylpiperidin-4-yl)sebacate
42. di-(1-methoxy-2,2,6,6-tetramethylpiperidin-4-yl)succinate
43. (1-cyclohexyloxy-2,2,6,6-tetramethylpiperidin-4-yl)-3,5-di.-t.butyl-4-hydroxybenzoate
44. 1-cyclohexyloxy-4-octadecanoyloxy-2,2,6,6-tetramethylpiperidine
45. di-(1-methoxy-2,2,6,6-tetramethylpiperidin-4-yl)isophthalate
46. di-(1-cyclohexyloxy-2,2,6,6-tetramethylpiperidin-4-yl)sebacate
47. di-(1-cyclohexyloxy-2,2,6,6-tetramethylpiperidin-4-yl)isophthalate
48. di-(1-heptyloxy-2,2,6,6-tetramethylpiperidin-4-yl)sebacate
49. di-[1-(alpha-methylbenzyloxy)-2,2,6,6-tetramethylpiperidin-4-yl]terephthalate
50. di-(1-ethoxy-2,2,6,6-tetramethylpiperidin-4-yl)sebacate
51. di-(1-cumyloxy-2,2,6,6-tetramethylpiperidin-4-yl)sebacate
52. 3,15-di-alpha-methylbenzyloxy-2,2,4,4,14,14,16,16-octamethyl-7,11,18,21-tetraoxa-3,15-diazatrispiro[5.2.2.5.2.2]heneicosane
53. 3,15-dicyclohexyloxy-2,2,4,4,14,14,16,16-octamethyl-7,11,18,21-tetraoxa-3,15-diazatrispiro[5.2.2.5.2.2]heneicosane
54. di-(1-cyclohexyloxy-2,2,6,6-tetramethylpiperidin-4-yl)succinate
55. di-[1-(alpha-methylbenzyloxy)-2,2,6,6-tetramethylpiperidin-4-yl]succinate
56. di-(1-nonyloxy-2,2,6,6-tetramethylpiperidin-4-yl)sebacate
57. di-(1-octadecyloxy-2,2,6,6-tetramethylpiperidin-4-yl)sebacate
58. di-(1-nonyloxy-2,2,6,6-tetramethylpiperidin-4-yl)succinate
59. di-[1-(1-methylcyclohexyloxy)-2,2,6,6-tetramethylpiperidin-4-yl]sebacate
60. di-[1-(3-cyclohexen-1-yloxy)-2,2,6,6-tetramethylpiperidin-4-yl]sebacate
61. di-(1-tert.butoxy-2,2,6,6-tetramethylpiperidin-4-yl)sebacate
62. di-(1-carbamoyloxy-2,2,6,6-tetramethylpiperidin-4-yl)n-butylmalonate
63. di-[1-(bicyclo-[4.4.0]-decyl-1-oxy)-2,2,6,6-tetramethylpiperidin-4-yl]sebacate
64. di-(1-n-butylcarbamoyloxy-2,2,6,6-tetramethylpiperidin-4-yl)phthalate
65. di-(1-n-butylcarbamoyloxy-2,2,6,6-tetramethylpiperidin-4-yl)n-butylmalonate
66. di-(1-phenylcarbamoyloxy-2,2,6,6-tetramethylpiperidin-4-yl)sebacate
67. 4-benzoyloxy-1-benzyloxy-2,2,6,6-tetramethylpiperidine
68. di-(1-octyloxy-2,2,6,6-tetramethylpiperidin-4-yl)sebacate
69. N,N',N'',N'''-tetrakis{2,4-bis[N-1-cyclohexyloxy-2,2,6,6-tetramethylpiperidin-4-yl)n-butylamino]-1,3,5-triazin-6-yl}-3,3'-ethylenediiminodipropylamine
70. 2,4,6-tris[N-6-cyclohexyloxy-2,2,6,6-tetramethylpiperidin-4-yl)-n-butylamino]-1,3,5-triazine
71. 2,4-bis[N-(1-cyclohexyloxy-2,2,6,6-tetramethylpiperidin-4-yl)-n-butylamino]-6-morpholino-1,3,5-triazine
72. 1-octyloxy variation of compound 69
73. N,N'-bis(1-cyclohexyloxy-2,2,6,6-tetramethylpiperidin-4-yl)—N,N'-bis{2,4-bis[N-(1-cyclohexyloxy-2,2,6,6-tetramethylpiperidin-4-yl)-n-butylamino]1,3,5-triazin-6-yl}hexamethylene diamine
74. N,N'-bis{2,4-bis[N-(1-cyclohexyloxy-2,2,6,6-tetramethylpiperidin-4-yl)-n-butylamino]-1,3,5-triazin-6-yl}piperazine
75. N-(1-cyclohexyloxy-2,2,6,6-tetramethylpiperidin-4-yl) succinimide
76. N-(1-methoxy-2,2,6,6-tetramethylpiperidin-4-yl) n-dodecyl succinimide
77. tetrakis(1-octyloxy-2,2,6,6-tetramethylpiperidin-4-yl)-1,2,3,4-butanetetracarboxylate
78. (1-methoxy-2,2,6,6-tetramethylpiperidin-4-yl)(1-octyloxy-2,2,6,6-tetramethylpiperidin-4-yl)sebacate.

The hydroxylamine derivatives of the instant invention are generally prepared by oxidizing the corresponding hindered amine with an appropriate peroxy compound such as hydrogen peroxide or tert-butyl hydroperoxide in the presence of a metal carbonyl or metal oxide catalyst followed by reduction of the oxyl intermediate formed to the desired N-hydroxy derivative, preferably by catalytic hydrogenation. Thereafter, the N-acyloxy derivatives are prepared by reacting the N-hydroxy hindered amine with the appropriate acid chloride, anhydride, isocyanate or substituted chloroformate. The catalytic hydrogenation can also be conducted in acetic anhydride to prepare the N-acetoxy derivative.

O-alkyl substituted N-hydroxy derivatives can be synthesized by several routes. The N-hydroxy derivative can be alkylated with sodium hydride and halogenated hydrocarbons such as benzyl bromide and ethyl iodide. N-methoxy variants can be prepared by thermolysis of a chlorobenzene solution of nitroxyl radical and di-tert-butyl peroxide. The product is formed by a coupling reaction between the nitroxyl radical and methyl radical generated from $\beta$-scission of a t-butoxy radical. Other N-alkoxy variants are synthesized by coupling nitroxyl radicals with hydrocarbon radicals generated from thermal decomposition of di-tert-butyl peroxide in the presence of hydrocarbon solvents such as cyclohexane, toluene, and ethylbenzene. Significant amounts of N-methoxy HALS are also formed in most of these reactions.

A preferred approach is the preparation of N-alkoxy hindered amines directly from hindered amines. For example, a mixture of 4-benzoyloxy-2,2,6,6-tetramethylpiperidine, aqueous t-butyl hydroperoxide, molybdenum oxide, and ethylbenzene gives a 90% yield of N-alphamethylbenzyloxy HALS. Molybdenum (VI) has been shown to increase the efficiency of both the oxidation of hindered amine to nitroxyl radical and the reaction of nitroxyl radicals with hydrocarbons. In addition, the N-hydroxy derivatives can be reacted with potassium t-butoxide and methyl acrylate to synthesize the N-alkoxy variants possessing an ester functionality.

The oxalates of formula N can be prepared by reacting (1-hydroxy-2,2,6,6-tetramethylpiperidin-4-yl)stearate, benzoate, and the like, with oxalylchloride, or for $G_1$ being —NH—G'—NH by reacting the appropriate 1-hydroxy-2,2,6,6-tetramethyl piperidine with the appropriate diisocyanate.

The hindered amine precursors are large commercially available or can be prepared by methods known in the art.

The key aspect of the resin systems of this invention is their capability to be fully cured under ambient conditions. The applicable resin enamels and lacquers (as identified hereinabove) which can be stabilized against light, moisture and oxygen in accordance with the invention are known. For example, applicable alkyd, acrylic, polyester and epoxide resins are described in S. Paul's "Surface Coatings: Science and Technology" (1985) at pages 70-310. Various acrylic and modified acrylic resins are described in H. Kittel's "Lehrbuch der Lacke und Beschichtungen", Vol. 1. Part 2, on pages 735 and 742 (Berlin 1972), and in "Lackkunstharze" (1977), by H. Wagner and H. F. Sarx, on pages 229-238. Typical crosslinkable polyester resins which can be stabilized against the action of light and moisture are described e.g. in H. Wagner and H. F. Sarx, op. cit., on pages 86-99. The unmodified and modified alkyd resins which can be stabilized against the action of light and moisture in accordance with the invention, are the conventional resins which are used in trade sales, maintenance and automotive refinish coatings. For example, such coatings are based on alkyd resins, alkyd/acrylic resins and alkyd/silicon resins (see H. Wagner and H. F. Sarx, op. cit., pages 99-123) optionally crosslinked by isocyanates or epoxy resins.

In addition various acrylic lacquer coating compositions are disclosed in U.S. Pat. No. 4,168,249. Other acrylic/alkyd resins with polyisocyanate additives are disclosed in U.S. Pat. No. 4,471,083; and acrylic resins containing either pendant amino ester groups or glycidyl groups are described in U.S. Pat. No. 4,525,521.

The ambient cured coatings stabilized in accordance with the invention are suitable both for metal finish coatings and solid shade finishes, especially in the case of retouching finishes. The lacquers stabilized in accordance with the invention are preferably applied in the conventional manner by two methods, either by the single-coat method or by the two-coat method. In the latter method, the pigment-containing base coat is applied first and a covering coat of clear lacquer applied over it. When used in two-coat finishes, the polyalkylpiperidine derivative can be incorporated in the clear coat or both in the clear coat and in the pigmented base coat.

The amount of polyalkylpiperidine derivative employed is 0.1 to 10% by weight, based on the solvent-free binder, preferably 0.5 to 5% by weight. The binders can be dissolved or dispersed in customary organic solvents or in water or can be solvent-free.

To attain maximum light stability, the concurrent use of other conventional light stabilizers can be advantageous. Examples are UV absorbers of the benzophenone, benztriazole, acrylic acid derivative, or oxalanilide type, or aryl-s-triazines or metal-containing light stabilizers, for example organic nickel compounds. In two-coat systems, these additional light stabilizers can be added to the clear coat and/or the pigmented base coat.

If such combinations are employed, the sum of all light stabilizers is 0.2 to 20% by weight, preferably 0.5 to 5% by weight, based on the film-forming resin.

Examples of the UV absorbers which may be used in the instant compositions in conjunction with the aforementioned piperidine compounds are:

(a) 2-(2'-Hydroxyphenyl)-benzotriazoles, for example, the 5'-methyl—, 3',5'-di-tert-butyl—, 5'-tert-butyl—, 5'-(1,1,3,3-tetramethylbutyl)—, 5-chloro-3',5'-di-tert-butyl—, 5-chloro-3'-tert-butyl-5'-methyl—, 3'-sec-butyl-5'-tert-butyl—, 4'-octoxy—, 3',5'-di-tert-amyl derivative.

(b) 2-Hydroxy-benzophenones, for example, the 4-hydroxy—, 4-methoxy—, 4-octoxy—, 4-decyloxy—, 4-dodecyloxy—, 4-benzyloxy, 4,2',4'-trihydroxy- and 2'-hydroxy-4,4'-dimethoxy derivative.

(c) Acrylates, for example, alpha-cyano-$\beta,\beta$-diphenylacrylic acid ethyl ester or isoctyl ester, alpha-carbomethoxy-cinnamic acid methyl ester, alpha-cyano-$\beta$-methyl-p-methoxy-cinnamic acid methyl ester or butyl ester, alpha-carbomethoxy-p-methoxy-cinnamic acid methyl ester, N-($\beta$-carbomethoxy-$\beta$-cyanovinyl)-2-methyl-indoline.

(d) Nickel compounds, for example, nickel complexes of 2,2'-thiobis-[4-(1,1,3,3-tetramethylbutyl)-phenol], such as the 1:1 or 1:2 complex, optionally with additional ligands such as n-butylamine, triethanolamine or N-cyclohexyl-diethanolamine, nickel dibutyldithiocarbamate, nickel salts of 4-hydroxy-3,5-di-tert-butylbenzylphosphonic acid monoalkyl esters, such as of the methyl, ethyl or butyl ester, nickel complexes of ketoximes such as of 2-hydroxy-4-methyl-phenyl undecyl ketonoxime, nickel complexes of 4-phenyl-4-lauroyl-5-hydroxy-pyrazol, optionally with additional ligands.

(e) Oxalic acid diamides, for example, 4,4'-di-octyloxyoxanilide, 2,2'-di-octyloxy-5,5'-di-tert-butyloxanilide, 2,2'-di-dodecyloxy-5,5'-di-tert-butyl-oxanilide, 2-ethoxy-2'-ethyl-oxanilide, N,N'-bis-(3-dimethylaminopropyl)-oxalamide, 2-ethoxy-5-tert-butyl-2'-ethyloxanilide and its mixture with 2-ethoxy-2'-ethyl-5,4'-di-tert-butyloxanilide and its mixtures of ortho- and paramethoxy- as well as of o- and p-ethoxy-disubstituted oxanilides.

(f) Hydroxyphenyl-5-triazines such as 2,6-bis-(2,4-dimethylphenyl)-4(2-hydroxy-4-octyloxyphenyl)-s-triazine or the corresponding 4(2,4-dihydroxyphenyl)- derivatives.

Of particular value in the instant compositions are the benzotriazoles of high molecular weight and low volatility such as 2-[2-hydroxy-3,5-di(alpha,alpha-dimethylbenzyl)-phenyl]-2H-benzotriazole, 2-(2-hydroxy-3,5-di-tert-octylphenyl)-2H-benzotriazole, 2-(2-hydroxy-3-alpha,alpha-dimethylbenzyl-5-tert-octyl-phenyl)-2H-benzotriazole, 2-(2-hydroxy-3-tert-octyl-5-alpha,alpha-di-methylbenzylphenyl)-2H-benzotriazole, 2-(2-hydroxy-3,5-di-tert-amylphenyl)-2H-benzotriazole, 2-[2-hydroxy-3-tert-butyl-5-(2-omega-hydroxy-octa-(ethyleneoxy)carbonyl)-ethylphenyl]-2H-benzotriazole, dodecylated 2-[2-hydroxy-5-methylphenyl)-2H-benzotriazole, 2-[2-hydroxy-3-tert.butyl-5-(2-octyloxycarbonyl)-ethylphenyl]-2H-benzotriazole and the 5-chloro compounds corresponding to each of the above named benzotriazoles.

Most preferably the benzotriazoles useful in the instant compositions are 2-[2-hydroxy-3,5-di(alpha,alpha-dimethylbenzyl)phenyl]-2H-benzotriazole, dodecylated 2-[2-hydroxy-5-methylphenyl)-2H-benzotriazole, 2-[2-hydroxy-3-tert-butyl-5-(2-(omega-hydroxy-octa-(ethyleneoxy)carbonyl)ethylphenyl]-2H-benzotriazole, 2-[2-hydroxy-3-tert.-butyl-5-(2-octyloxycarbonyl)-ethylphenyl]-2H-benzotriazole and 5-chloro-2-[2-hydroxy-3-tert.butyl-5-(2-octyloxycarbonyl)ethylphenyl]-2H-benzotriazole.

A preferred embodiment of the instant invention pertains to stabilized compositions comprising
(a) a resin system as defined hereinabove,
(b) a NOR$_1$-substituted 2,2,6,6-tetraalkylpiperidine compound, and
(c) a UV absorber selected from the group consisting of the benzophenones, benzotriazoles, acrylic acid derivatives, organic nickel compounds, aryl-s-triazines and oxanilides.

Further ingredients which the enamels or coatings can contain are antioxidants, for example those of the sterically hindered phenol derivative type, phosphorus compounds, such as phosphites, phosphines or phosphonites, conventional hindered amine light stabilizers, plasticizers, levelling assistants, hardening catalysts, thickeners, dispersants or adhesion promoters.

A further preferred embodiment of the instant invention is a stabilized composition containing components (a), (b) and (c) described above which additionally contains as component (d) a phosphite or phosphonite.

The amount of phosphite or phosphonite d) which is used in the instant compositions is from 0.05 to 2% by weight, preferably from 0.1 to 1% by weight, based on the film forming resin. In two-coat systems, these stabilizers may be added to the clear coat and/or the base coat.

Typical phosphite and phosphonites include triphenyl phosphite, diphenylalkyl phosphites, phenyldialkyl phosphites, tri-(nonylphenyl)phosphite, trilauryl phosphite, trioctadecyl phosphite, di-stearyl-pentaerythritol diphosphite, tris-(2,4-di-tert.butylphenyl) phosphite, di-isodecylpentaerythritol diphosphite, di-(2,4-di-tert.butylphenyl)pentaerythritol diphosphite, tristearylsorbitol triphosphite, tetrakis-(2,4-di-tert.butylphenyl)-4,4'-diphenylylenediphosphonite.

The stabilizers are needed to impart greater retention of durability to the ambient cured enamels (as measured by 20° gloss, distinction of image, cracking or chalking); the enamel should not yellow on curing and further color change on exposure to light should be minimized; the stabilizers should be soluble in the organic solvents normally used in coating applications such as methyl amyl ketone, xylene, n-hexyl acetate, alcohol and the like.

The instant hindered amine light stabilizers substituted on the hindered N-atom by an 0-substituted moiety fulfill each of these requirements and provide individually or in combination with a UV-absorber outstanding light stabilization protection to the ambient cured coatings.

The following examples describe the inventive use of substituted polyalkylpiperidine derivatives in various ambient curable resin systems. Parts and percentages are by weight.

EXAMPLE 1

Stabilization of Tung Oil Phenolic Varnish

Pieces of 1.27 cm × 20.32 cm × 30.48 cm western red cedar panels having a fine radial cut are used to test a commercially available tung oil phenolic varnish (supplied by McCloskey). One half of each panel is coated with two coats of the unstabilized varnish. An equal amount of varnish containing 5% (by weight based on resins solids) of light stabilizers is applied to the other half of the panel in two coats. After storage for 2 weeks at ambient temperature, the wood panels are exposed outdoors at an angle of 45° S for a period of 8 months. The 60° gloss of each half of the panel is measured at the top, middle, and bottom portion of the panel and averaged (ASTM D 523). Due to the lack of homogeneity of wood substrates, the gloss retention of the same varnish tends to differ slightly from panel to panel. Thus, the application of an unstabilized control varnish to every panel allows for a more meaningful measurement of the improvement in gloss due to the presence of the light stabilizer.

| Compound | 60° Gloss Retention (%) | | |
| --- | --- | --- | --- |
| | Unstabilized | Stabilized | Gloss Improvement |
| 3 | 24.2 | 46.7 | 22.5 |
| A | 28.9 | 39.0 | 10.1 |

A - bis(1,2,2,6,6-pentamethyl-4-piperidinyl)sebacate

EXAMPLE 2

Stabilization of an Aromatic Urethane Varnish

A sample of a commercial aromatic urethane varnish (Flecto-Varathane #90) is tested in the same method as described in Example 1. After outdoor exposure at an angle of 45° S for a period of 5 months, the 60° gloss retention values of the unstabilized and stabilized portions of the panel are determined.

| Compound | Conc. (% by wt.) | 60° Gloss Retention (%) Unstabilized | Stabilized | Gloss Improvement |
|---|---|---|---|---|
| A | 7 | 45.2 | 59.2 | 14.0 |
| 33 | 7 | 52.5 | 63.6 | 11.1 |
| 34 | 7 | 42.5 | 62.1 | 19.6 |
| B/A | 3.5/3.5 | 39.8 | 48.0 | 8.2 |
| B/33 | 3.5/3.5 | 44.5 | 64.0 | 19.5 |
| B/34 | 3.5/3.5 | 45.6 | 65.6 | 20.5 |

B is 2-(2-hydroxy-3,5-di-tert-amylphenyl)-2H-benzotriazole

EXAMPLE 3

Stabilization of a White Two-Component Polyester Urethane Gloss Enamel

A white polyester was formulated as shown below

| | Parts |
|---|---|
| Component I | |
| Desmophen 670-90 (polyester polyol from Mobay Corp) | 132.4 |
| Titanium Dioxide | 198.6 |
| Cellosolve Acetate | 98.9 |
| Sand Mill | |
| Desmophen 670-90 | 94.98 |
| Flow Aid | 0.28 |
| Tertiary Amine | 0.015 |
| Cellosolve Acetate | 332.6 |
| Component II | |
| Desmodur N-100 (polyisocyanate from Mobay Corp.) | 93.9 |
| Cellosolve Acetate | 58.7 |

This material is spray applied at a dry film thickness of 1.5-2.0 mil onto Bonderite 40 cold rolled steel panels that have been previously primed with a commercial epoxy polyamide maintenance primer (Sherwin-Williams Tile Clad II). Prior to application, the indicated amounts of hindered amine derivatives (based on resin solids) are added to the paint. After ambient storage for a period of two weeks, three panels of each formulation are exposed outdoors at an angle of 45° S for a period of 9 months. Thereafter, the 20° gloss retention is determined (ASTM D 523-80) at the top, middle and bottom portions of each panel. Thus, the average values for nine gloss retention measurements for each triplicate set of panels are reported below

| Additive | Conc. (% by wt.) | 20° Gloss Retention (%) |
|---|---|---|
| A | 1 | 55 |
| A | 2 | 64 |
| 3 | 1 | 67 |
| 26 | 1 | 69 |

EXAMPLE 4

Stabilization of Acrylic Alkyd Refinish Enamel

A commercially available acrylic alkyd enamel pigmented with non-leafing aluminum pigment and tinted a light blue is stabilized with the indicated amount of ultraviolet light absorber and hindered amine derivative (by weight on resin solids) and then spray applied onto Bonderite 40 panels primed with an alkyd primer. After the coating is allowed to cure at room temperature for 14 days, the panels are exposed outdoors at an angle of 5° S for a period of 8 months. The 20° gloss of the panels is measured, as reported below.

| Additive | Conc. (% by wt.) | 20° Gloss |
|---|---|---|
| C/29 | 3/2 | 36 |
| C/38 | 3/2 | 31 |
| C/40 | 3/2 | 31 |
| C/46 | 3/2 | 36 |

C - 2-[2-hydroxy-3-tert.butyl-5-(2-(omega-hydroxy-octa-(ethyleneoxy)carbonyl-ethylphenyl]-2H-benzotriazole

EXAMPLE 5

Stabilization of a Medium Oil Alkyd Enamel

A medium oil alkyd enamel pigmented with non-leafing aluminum pigment and tinted light blue is stabilized with the indicated amounts of ultraviolet light absorber and hindered amine derivative, and then spray applied onto cold rolled steel panels primed with an epoxy primer. After the coating is allowed to cure at room temperature for 2 weeks, the panels are exposed for accelerated weathering in a Xenon Arc Weatherometer for 840 hours. The 20° gloss values of the panels are determined before and after exposure and indicated below in terms of % gloss retention

| Additive | Conc. (% by wt.) | 20° Gloss Retention (%) |
|---|---|---|
| C/A | 3/2 | 18.9 |
| C/1 | 3/2 | 26.4 |
| C/32 | 3/2 | 28.8 |
| C/36 | 3/2 | 31.7 |
| C/37 | 3/2 | 42.9 |

C - 2-[2-hydroxy-3-tert.butyl-5-(2-(omega-hydroxy-octa-(ethyleneoxy)carbonyl-ethylphenyl]-2H-benzotriazole

EXAMPLE 6

Stabilization of an Acrylic Alkyd Crosslinked with an Aliphatic Isocyanate Refinish Enamel A silver metallic acrylic alkyd enamel hardened with an aliphatic isocyanate is stabilized with the indicated amounts of ultraviolet light absorber and hindered amine derivative (by weight on total resin solids) and then spray applied onto Bonderite 40 panels primed with a black alkyd primer. After the coatings are aged at ambient temperature for 2 weeks, the panels are exposed in an Xenon Arc Weatherometer for 1550 hours. The 20° gloss values of the unexposed and exposed panels are determined and reported below in terms of % gloss retention.

| Additive | Conc. (% by wt.) | 20° Gloss Retention (%) |
|---|---|---|
| C/A | 3/2 | 20.7 |
| C/3 | 3/2 | 25.7 |
| C/22 | 3/2 | 24.3 |
| C/36 | 3/2 | 29.2 |
| C/38 | 3/2 | 38.9 |

EXAMPLE 7

The following alkyd paint formulations are prepared.

| | White (W) | Yellow (Y) | Blue (B) |
|---|---|---|---|
| Aroplaz 1445 M-50 (binder only) | 45.0 | 57.73 | 58.27 |

-continued

|  | White (W) | Yellow (Y) | Blue (B) |
|---|---|---|---|
| (alkyd resin from NL Industries) | | | |
| TiO$_2$ | 45.0 | 20.82 | 4.26 |
| Irgalite GS (yellow pigment from Ciba-Geigy) | — | 7.3 | — |
| Phthalocyanine blue | — | — | 1.41 |
| ketoxime (antiskinning agent) | 0.17 | 0.07 | 0.014 |
| Ionic antifloat compound | — | — | 0.05 |
| 24% Pb as naphthenate | 0.94 | 1.30 | 1.30 |
| 6% Co as naphthenate | 0.36 | 0.50 | 0.50 |
| 6% Mn as naphthenate | 0.45 | 0.60 | 0.60 |
| Xylene | 35.0 | 48.4 | 45.1 |
| Mineral Spirits | 60.0 | 64.49 | 64.11 |

The formulations are stabilized with the indicated materials in the indicated concentrations (by weight on total resin solids) and sprayed onto cold rolled steel panels primed with an electrocoated epoxy primer. The coating is allowed to cure overnight at room temperature and the panels are then exposed in Florida at an angle of 45° South. 60° gloss, distinction of image (DI) (Hunter Associates Apparatus) and color change based on Yellowness Index values are determined as tabulated below.

| Additive | Conc. (% by wt.) | Paint | Florida Exposure (Months) | | | | | | | | | | |
|---|---|---|---|---|---|---|---|---|---|---|---|---|---|
| | | | 60° Gloss | | | | DI | | | | Color Change | | |
| | | | 0 | 9 | 12 | 15 | 0 | 9 | 12 | 15 | 9 | 12 | 15 |
| — | — | W | 61 | 30 | 29 | 30 | 63 | 6 | 18 | 25 | 3.0 | 2.7 | 4.0 |
| B/A | 1.5/1.5 | W | 61 | 28 | 27 | 35 | 55 | 8 | 7 | 19 | 4.2 | 4.4 | 5.4 |
| B/3 | 1.5/1.5 | W | 63 | 43 | 34 | 43 | 80 | 52 | 24 | 38 | 3.5 | 3.9 | 4.8 |
| — | — | Y | 81 | 30 | 15 | 14 | 84 | 78 | 12 | 7 | 11.0 | 12.0 | 13.0 |
| B/A | 1.5/1.5 | Y | 83 | 41 | 25 | 21 | 78 | 58 | 36 | 12 | 8.9 | 11.0 | 12.0 |
| B/3 | 1.5/1.5 | Y | 83 | 50 | 31 | 25 | 82 | 73 | 60 | 24 | 8.0 | 10.0 | 12.0 |
| — | — | B | 86 | 33 | 15 | 11* | 84 | 61 | 10 | 0 | 7.6 | 11.0 | 10.0 |
| B/A | 1.5/1.5 | B | 83 | 63 | 58 | 44 | 80 | 69 | 68 | 59 | 2.0 | 2.6 | 3.3 |
| B/3 | 1.5/1.5 | B | 85 | 63 | 54 | 45 | 86 | 79 | 78 | 64 | 2.0 | 4.0 | 4.3 |

*cracking observed

The test data in Examples 1–8 thus demonstrate the improved stabilization provided to ambient cured coatings by the hindered amine derivatives of this invention, individually and in combination with UV absorbers.

EXAMPLE 8

Stabilization of a Thermoplastic Acrylic Lacquer

A commercially available light blue metallic thermoplastic acrylic lacquer is stabilized with 2% each of UV absorber and hindered amine (by weight on total resin solids) and then spray applied onto Bonderite 40 panels primed with an alkyd primer. After storage at ambient temperature for 2 weeks, the panels are exposed in an Xenon Arc Weatherometer for 1250 hours. The 20° gloss retention of the panels are reported below.

| Additive | 20° Gloss Retention (%) |
|---|---|
| D/A | 11 |
| D/3 | 29 |
| D/19 | 35 |
| D/29 | 40 |
| D/32 | 21 |
| D/36 | 23 |
| D/38 | 21 |
| D/45 | 24 |
| D/46 | 27 |

D - 2-(2-hydroxy-3,5-di(alpha,alpha-dimethylbenzyl)phenyl)-2H-benzotriazole

EXAMPLE 9

The acrylic alkyd enamel of Example 4 pigmented with non-leafing aluminum pigment is stabilized with the indicated amount of light stabilizers (by weight on resin solids) and then spray applied onto Bonderite 40 panels primed with an alkyd primer. After the coating is allowed to cure at ambient temperature for 14 days, the panels are exposed in the QUV weatherometer. The 60° gloss values of the panels at various intervals are listed below.

| Additive | Conc. (% by wt.) | 60° Gloss (at hours) | | | | |
|---|---|---|---|---|---|---|
| | | 0 | 208 | 433 | 593 | 712 |
| — | — | 87 | 38 | 25 | 19 | 13* |
| A | 2 | 88 | 64 | 31 | 25 | 21 |
| 48 | 2 | 89 | 69 | 45 | 37 | 31 |
| 68 | 2 | 85 | 62 | 43 | 32 | 24 |
| C/A | 2/2 | 87 | 65 | 45 | 41 | 30 |
| C/48 | 2/2 | 87 | 77 | 62 | 54 | 45 |
| C/68 | 2/2 | 91 | 79 | 53 | 46 | 41 |

*cracking

The data in Examples 1–9 thus clearly illustrate the beneficial stabilization performance characteristics of the instant compounds in ambient cured coatings.

What is claimed is:

1. An ambient curable, stabilized composition comprising
   (a) a resin selected from the group consisting of unmodified or modified alkyd resins, acrylic resins, acrylic alkyd resins, polyester resins and crosslinked epoxide resins; and
   (b) an effective oxidative and light stabilizing amount of an O-substituted N-hydroxyl hindered amine derivative corresponding to one of formulae A to P

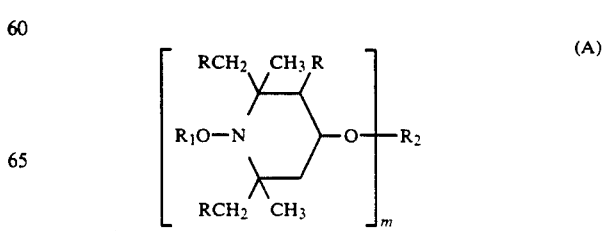

(A)

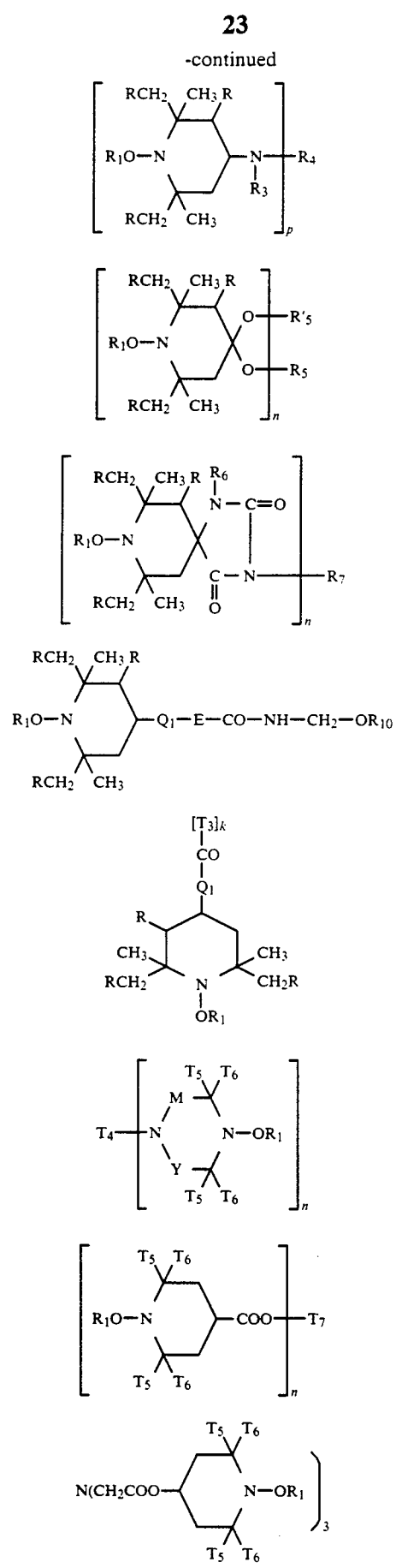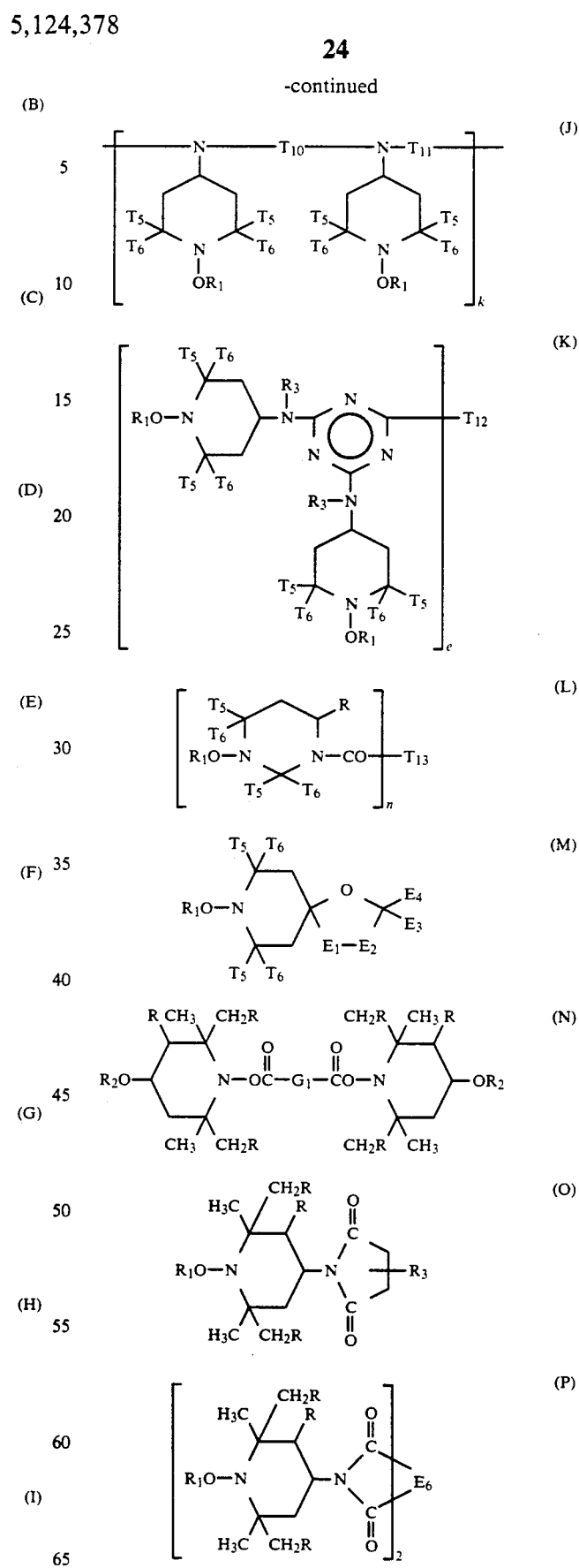
wherein
R is hydrogen or methyl, $R_1$ is independently $C_1$–$C_{18}$ alkyl, $C_2$–$C_{18}$ alkenyl, $C_2$–$C_{18}$ alkynyl, $C_5$–$C_{12}$ cycloalkyl, $C_6$–$C_{10}$ bicycloalkyl, $C_5$–$C_8$ cycloalkenyl, $C_6$–$C_{10}$ aryl, $C_7$–$C_9$ aralkyl, $C_7$–$C_9$ aralkyl substituted by alkyl or aryl, or

wherein D is $C_1$–$C_{18}$ alkyl, $C_1$–$C_{18}$ alkoxy, phenyl, phenyl substituted by hydroxy, alkyl or alkoxy, or amino or amino mono- or disubstituted by alkyl or phenyl;

m is 1–4, when m is 1, $R_2$ is hydrogen, $C_1$–$C_{18}$ alkyl optionally interrupted by one or more oxygen atoms, $C_2$–$C_{12}$ alkenyl, $C_6$–$C_{10}$ aryl, $C_7$–$C_{18}$ aralkyl, glycidyl, a monovalent acyl radical of an aliphatic, cycloaliphatic, araliphatic or aromatic carboxylic acid, or of a carbamic acid

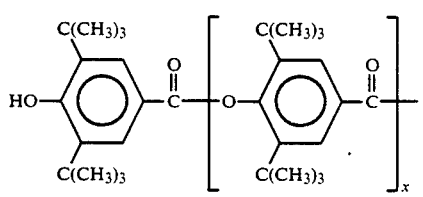

wherein x is 0 or 1, or

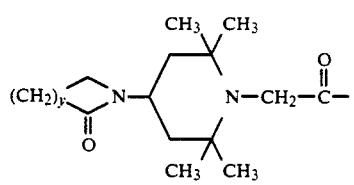

wherein y is 2–4;

when m is 2, $R_2$ is $C_1$–$C_{12}$ alkylene, $C_4$–$C_{12}$ alkenylene, xylylene, a divalent acyl radical of an aliphatic, cycloaliphatic, araliphatic or aromatic dicarboxylic acid or of a dicarbamic acid, when m is 3, $R_2$ is a trivalent acyl radical of an aliphatic, unsaturated aliphatic, cycloaliphatic, or aromatic tricarboxylic acid;

when m is 4, $R_2$ is a tetravalent acyl radical of a saturated or unsaturated aliphatic or aromatic tetracarboxylic acid;

p is 1, 2 or 3, $R_3$ is hydrogen, $C_1$–$C_{12}$ alkyl, $C_5$–$C_7$ cycloalkyl, $C_7$–$C_9$ aralkyl, $C_2$–$C_{18}$ alkanoyl, $C_3$–$C_5$ alkenoyl or benzoyl;

when p is 1, $R_4$ is hydrogen, $C_1$–$C_{18}$ alkyl, $C_5$–$C_7$ cycloalkyl, $C_2$–$C_8$ alkenyl unsubstituted or substituted by a cyano, carbonyl or carbamide group, aryl, aralkyl, or it is glycidyl, a group of the formula —CH$_2$—CH(OH)—Z or of the formula —CONH—Z wherein Z is hydrogen, methyl or phenyl; or a group of the formulae

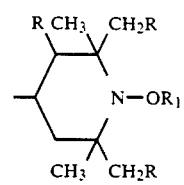

or

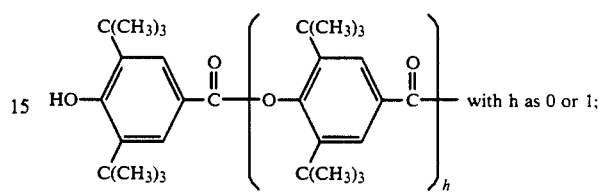

or $R_3$ and $R_4$ together when p is 1 can be alkylene of 4 to 6 carbon atoms or 2-oxapolyalkylene or the cyclic acyl radical of an aliphatic or aromatic 1,2- or 1,3-dicarboxylic acid, when p is 2, $R_4$ is a direct bond or is $C_1$–$C_{12}$ alkylene, $C_6$–$C_{12}$ arylene, xylylene, a —CH$_2$CH(OH)—CH$_2$ group, or a group —CH$_2$—CH(OH)—CH$_2$—O—X—O—CH$_2$—CH(OH)—CH$_2$— wherein X is $C_2$–$C_{10}$ alkylene, $C_6$–$C_{15}$ arylene or $C_6$–$C_{12}$ cycloalkylene; or, provided that $R_3$ is not alkanoyl, alkenoyl or benzoyl, $R_4$ can also be a divalent acyl radical of an aliphatic, cycloaliphatic or aromatic dicarboxylic acid or dicarbamic acid, or can be the group —CO—; or $R_4$ is

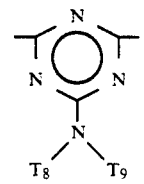

where $T_8$ and $T_9$ are independently hydrogen, alkyl of 1 to 18 carbon atoms, or $T_8$ and $T_9$ together are alkylene of 4 to 6 carbon atoms or 3-oxapentamethylene, when p is 3, $R_4$ is 2,4,6-triazinyl, n is 1 or 2, when n is 1, $R_5$ and $R'_5$ are independently $C_1$–$C_{12}$ alkyl, $C_2$–$C_{12}$ alkenyl, $C_7$–$C_{12}$ aralkyl, or $R_5$ is also hydrogen, or $R_5$ and $R'_5$ together are $C_2$–$C_8$ alkylene or hydroxyalkylene or $C_4$–$C_{22}$ acyloxyalkylene;

when n is 2, $R_5$ and $R'_5$ together are (—CH$_2$)$_2$C(CH$_2$—)$_2$;

$R_6$ is hydrogen, $C_1$–$C_{12}$ alkyl, allyl, benzyl, glycidyl or $C_2$–$C_6$ alkoxyalkyl;

when n is 1, $R_7$ is hydrogen, $C_1$–$C_{12}$ alkyl, $C_3$–$C_5$ alkenyl, $C_7$–$C_9$ aralkyl, $C_5$–$C_7$ cycloalkyl, $C_2$–$C_4$ hydroxyalkyl, $C_2$–$C_6$ alkoxyalkyl, $C_6$–$C_{10}$ aryl, glycidyl, a group of the formula —(CH$_2$)$_6$—COO—Q or of the formula —(CH$_2$)$_t$—O—CO—Q wherein t is 1 or 2, and Q is $C_1$–$C_4$ alkyl or phenyl; or when n is 2, $R_7$ is $C-C_{12}$ alkylene, $C_6-C_{12}$ arylene, a group —CH$_2$CH(OH)—CH$_2$—O—X—O—CH$_2$—CH(OH)—CH$_2$— wherein X is $C_2-C_{10}$ alkylene, $C_6-C_{15}$ arylene or $C_6-C_{12}$ cycloalkylene, or a group —CH$_2$CH(OZ')CH$_2$-(OCH$_2$—CH(OZ')CH$_2$)$_2$— wherein Z' is hydrogen, $C_1-C_{18}$ alkyl, allyl, benzyl, $C_2-C_{12}$ alkanoyl or benzoyl;

$Q_1$ is —N($R_8$)— or —O—;

E is $C_1-C_3$ alkylene, the group —CH$_2$—CH($R_9$)—O— wherein $R_9$ is hydrogen, methyl or phenyl, the group —(CH$_2$)$_3$—NH— or a direct bond;

$R_{10}$ is hydrogen or $C_1-C_{18}$ alkyl;

$R_8$ is hydrogen, $C_1-C_{18}$ alkyl, $C_5-C_7$ cycloalkyl, $C_7-C_{12}$ aralkyl, cyanoethyl, $C_6-C_{10}$ aryl, the group —CH$_2$—CH($R_9$)—OH wherein $R_9$ has the meaning defined above; a group of the formula

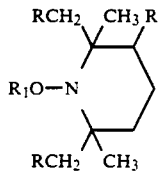

or a group of the formula

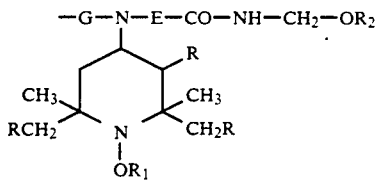

wherein G is $C_2-C_6$ alkylene or $C_6-C_{12}$ arylene; or $R_8$ is a group —E—CO—NH—CH$_2$—OR$_{10}$;

$T_3$ is ethylene or 1,2-propylene, or is the repeating structural unit derived from an alpha-olefin copolymer with an alkyl acrylate or methacrylate;

k is 2 to 100;

$T_4$ has the same meaning as $R_4$ when p is 1 or 2, $T_5$ is methyl, $T_6$ is methyl or ethyl, or $T_5$ and $T_6$ together are tetramethylene or pentamethylene;

M and Y are independently methylene or carbonyl;

$T_7$ is the same as $R_7$;

$T_{10}$ and $T_{11}$ are independently alkylene of 2 to 12 carbon atoms, or $T_{11}$ is

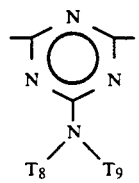

$T_{12}$ is piperazinyl, —NR$_{11}$—(CH$_2$)$_d$—NR$_{11}$— or

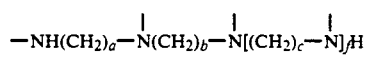

where $R_{11}$ is the same as $R_3$ or is also

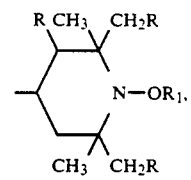

a, b and c are independently 2 or 3, and f is 0 or 1, e is 2, 3 or 4;

$T_{13}$ is the same as $R_2$ with the proviso that $T_{13}$ cannot be hydrogen when n is 1;

$E_1$ and $E_2$, being different, each are —CO— or —N($E_5$)— wherein $E_5$ is hydrogen, $C_1-C_{12}$ alkyl or $C_4-C_{22}$ alkoxycarbonylalkyl;

$E_3$ is hydrogen, alkyl of 1 to 30 carbon atoms, phenyl, naphthyl, said phenyl or said naphthyl substituted by chlorine or by alkyl of 1 to 4 carbon atoms, or phenylalkyl of 7 to 12 carbon atoms, or said phenylalkyl substituted by alkyl of 1 to 4 carbon atoms;

$E_4$ is hydrogen, alkyl of 1 to 30 carbon atoms, phenyl, naphthyl or phenylalkyl of 7 to 12 carbon atoms, or $E_3$ and $E_4$ together are polymethylene of 4 to 17 carbon atoms, or said polymethylene substituted by up to four alkyl groups of 1 to 4 carbon atoms;

$R_2$ of formula (N) is a previously defined when m is 1;

$G_1$ is a direct bond, $C_1-C_{12}$ alkylene, phenylene or —NH—G'—NH wherein G' is $C_1-C_{12}$ alkylene; and $E_6$ is an aliphatic or aromatic tetravalent radical.

2. The composition according to claim 1 wherein the compound of component (b) is selected from the group consisting of di-(1-acetoxy-2,2,6,6-tetramethylpiperidin-4-yl)phthalate, di-(1-acetoxy-2,2,6,6-tetramethylpiperidin-4-yl)isophthalate, di-(1-acetoxy-2,2,6,6-tetramethylpiperidin-4-yl) sebacate, di-(1-acetoxy-2,2,6,6-tetramethylpiperidin-4-yl) succinate, di-(1-acetoxy-2,2,6,6-tetramethylpiperidin-4-yl) adipate, di-(1-acetoxy-2,2,6,6-tetramethylpiperidin-4-yl) n-butylmalonate, di-(1-acetoxy-2,2,6,6-tetramethylpiperidin-4-yl) 2,2-diethylmalonate, poly-{[6-[(1,1,3,3-tetramethylbutyl)-imino]-1,3,5-triazine-2,4-diyl][2-(1-acetoxy-2,2,6,6-tetramethylpiperidyl)-imino]-hexamethylene-[4-(1-acetoxy-2,2,6,6-tetramethylpiperidyl)-imino]}, 1,4-diacetoxy-2,2,6,6-tetramethylpiperidine, 1-acetoxy-4-hydroxy-2,2,6,6-tetramethylpiperidine, (1-acetoxy-2,2,6,6-tetramethylpiperidin-4-yl)-4-hydroxy-3,5-di-tert.butylbenzoate, 2-(4-hydroxy-3,5-di-tert.butylbenzyl)-2-(1-acetoxy-2,2,6,6-tetramethylpiperidin-4-yl) n-butylmalonate, N-(1-acetoxy-2,2,6,6-tetramethylpiperidin-4-yl)-N-(n-butyl)-4-(4-hydroxy-3,5-di-tert.butylbenzoyloxy)-3,5-di-tert.butylbenzamide, 1,6-di-(N-acetyl-N-(1-acetoxy-2,2,6,6-tetramethylpiperidin-4-yl)]aminohexane, di-(1-acetoxy-2,2,6,6-tetramethylpiperidin-4-yloxy)hexane-1,6-dicarbamate, 1-acetoxy-4-(N-acetyl-N-n-dodecylamino)-2,2,6,6tetramethylpiperidine, di-(1-propionoxy-2,2,6,6-tetramethylpiperidin-4-yl) succinate, di-(4-n-octadecanoyloxy-2,2,6,6-tetramethylpiperazin-1-yl)oxalate,
1,4-di-(2-ethylhexanoyloxy)-2,2,6,6-tetramethylpiperidine,
1,4-di-(4-hydroxy-3,5-di-tert.butylbenzoyloxy)-2,2,6,6-tetramethylpiperidine,
di-(1-benzoyloxy-2,2,6,6-tetramethylpiperidin-4-yl) sebacate,
1-benzoyloxy-4-(N-n-butyl-N-benzoylamino)-2,2,6,6-tetramethylpiperidine,
1-benzoyloxy-2,2,6,6-tetramethylpiperdin-4-yl)azepin-2-one,
[1-benzoyloxy-1'-benzyloxy-di-(2,2,6,6-tetramethylpiperidin-4-yl)]isophthalate,
1,4-di-(4-hydroxy-3,5-di-tert-butylbenzoyloxy)-2,2,6,6-tetramethylpiperidine,
n-butyl-(4-benzoyloxy-2,2,6,6-tetramethylpiperidin-4-yl)carbonate,
1-carbamoyloxy-4-benzoyloxy-2,2,6,6-tetramethyl piperidine,
di(1-carbamoyloxy-2,2,6,6-tetramethylpiperidin-4-yl)sebacate,
di-(1-n-butylcarbamoyloxy-2,2,6,6-tetramethylpiperidin-4-yl)2,2-diethylmalonate,
di-(4-benzoyloxy-2,2,6,6-tetramethylpiperidin-1-yl)-2,4,4-trimethylhexane-1,6-dicarbamate,
alpha,alpha -(di-1-ethoxy-2,2,6,6-tetramethylpiperidin-4-yloxy)-p-xylene,
4-benzyloxy-1-ethoxy-2,2,6,6-tetramethylpiperidine,
1,4-dibenzyloxy-2,2,6,6-tetramethylpiperidine,
alpha,alpha'-(di-1-benzyloxy-2,2,6,6-tetramethylpiperidin-4-yloxy)-p-xylene,
di-(1-benzyloxy-2,2,6,6-tetramethylpiperidin-4-yl) sebacate,
4-benzoyloxy-1-(alpha-methylbenzyloxy)-2,2,6,6-tetramethylpiperidine,
di-[1-(alpha-methylbenzyloxy)-2,2,6,6-tetramethylpiperidin-4-yl] sebacate,
1,4-dimethoxy-2,2,6,6-tetramethylpiperidine,
4-benzoyloxy-1-methoxy-2,2,6,6-tetramethylpiperidine,
di-(1-methoxy-2,2,6,6-tetramethylpiperidin-4-yl)sebacate,
di-(1-methoxy-2,2,6,6-tetramethylpiperidin-4-yl)succinate,
(1-cyclohexyloxy-2,2,6,6-tetramethylpiperidin-4-yl)-3,5-di-t.butyl-4-hydroxybenzoate,
1-cyclohexyloxy-4-octadecanoyloxy-2,2,6,6-tetramethylpiperidine,
di-(1-methoxy-2,2,6,6-tetramethylpiperidin-4-yl)isophthalate,
di-(1-cyclohexyloxy-2,2,6,6-tetramethylpiperidin-4-yl)sebacate,
di-(1-cyclohexyloxy-2,2,6,6-tetramethylpiperidin-4-yl)isophthalate,
di-(1-heptyloxy-2,2,6,6-tetramethylpiperidin-4-yl)sebacate,
di-[1-(alpha-methylbenzyloxy)-2,2,6,6-tetramethylpiperidin-4-yl]terephthalate,
di-(1-ethoxy-2,2,6,6-tetramethylpiperidin-4-yl)sebacate,
di-(1-cumyloxy-2,2,6,6-tetramethylpiperidin-4-yl)sebacate,
3,15-di-alpha-methylbenzyloxy-2,2,4,4,14,14,16,16-octamethyl-7,11,18,21-tetraoxa-3,15-diazatrispiro[5.2.2.5.2.2]heneicosane,
3,15-dicyclohexyloxy-2,2,4,4,14,14,16,16-octamethyl-7,11,18,21-tetraoxa-3,15-diazatrispiro[5.2.2.5.2.2-]heneicosane,
di-(1-cyclohexyloxy-2,2,6,6-tetramethylpiperidin-4-yl)succinate,
di-[1-(alpha-methylbenzyloxy)-2,2,6,6-tetramethylpiperidin-4-yl]succinate,
di-(1-nonyloxy-2,2,6,6-tetramethylpiperidin-4-yl)sebacate,
di-(1-octadecyloxy-2,2,6,6-tetramethylpiperidin-4-yl)sebacate,
di-(1-nonyloxy-2,2,6,6-tetramethylpiperidin-4-yl)succinate,
di-[1-(1-methylcyclohexyloxy)-2,2,6,6-tetramethylpiperidin-4-yl]sebacate,
di-[1-(3-cyclohexen-1-yloxy)-2,2,6,6-tetramethylpiperidin-4-yl]sebacate,
di-(1-tert.butoxy-2,2,6,6-tetramethylpiperidin-4-yl)sebacate,
di-(1-carbamoyloxy-2,2,6,6-tetramethylpiperidin-4-yl)n-butylmalonate,
di-[1-(bicyclo-[4.4.0]-decyl-1-oxy)-2,2,6,6-tetramethylpiperidin-4-yl]sebacate,
di-(1-n-butylcarbamoyloxy-2,2,6,6-tetramethylpiperidin-4-yl)phthalate,
di-(1-n-butylcarbamoyloxy-2,2,6,6-tetramethylpiperidin-4-yl)n-butylmalonate,
di-(1-phenylcarbamoyloxy-2,2,6,6-tetramethylpiperidin-4-yl)sebacate,
4-benzoyloxy-1-benzyloxy-2,2,6,6-tetramethylpiperidine,
di-(1-octyloxy-2,2,6,6-tetramethylpiperidin-4-yl)sebacate,
N,N',N'',N'''-tetrakis{2,4-bis[N-1-cyclohexyloxy-2,2,6,6-tetramethylpiperidin-4-yl)n-butylamino]1,3,5-triazin-6-yl}-3,3'-ethylenediiminodipropylamine,
2,4,6-tris[N-6-cyclohexyloxy-2,2,6,6-tetramethylpiperidin-4-yl)-n-butylamino]-1,3,5-triazine,
2,4-bis[N-(1-cyclohexyloxy-2,2,6,6-tetramethylpiperidin-4-yl)-n-butylamino]-6-morpholino-1,3,5triazine,
N,N'-bis(1-cyclohexyloxy-2,2,6,6-tetramethylpiperidin-4-yl)-N,N'-bis{2,4-bis[N-(1-cyclohexyloxy-2,2,6,6-tetramethylpiperidin-4-yl)-n-butylamino]-1,3,5-triazin-6-yl}hexamethylene diamine,
N,N'-bis{2,4-bis[N-(1-cyclohexyloxy-2,2,6,6-tetramethylpiperidin-4-yl)-n-butylamino]-1,3,5-triazin-6-yl}[piperazine,
N-(1-cyclohexyloxy-2,2,6,6-tetramethylpiperidin-4-yl) succinimide,
N-(1-methoxy-2,2,6,6-tetramethylpiperidin-4-yl) n-dodecyl succinimide,
tetrakis(1-octyloxy-2,2,6,6-tetramethylpiperidin-4-yl)-1,2,3,4-butanetetracarboxylate and octyloxy-2,2,6,6-tetramethylpiperidin-4-yl)sebacate.

3. The composition of claim 2, wherein said compound is di-(1-acetoxy-2,2,6,6-tetramethylpiperidin-4-yl)-sebacate.

4. The composition of claim 2, wherein said compound is alpha,alpha'-(di-1-ethoxy-2,2,6,6-tetramethylpiperidin-4-yloxy)-p-xylene.

5. The composition of claim 2, wherein said compound is 1,4-dibenzyloxy-2,2,6,6-tetramethylpiperidine.

6. The composition of claim 2, wherein said compound is di-(1-benzyloxy-2,2,6,6-tetramethylpiperidin-4-yl) sebacate.

7. The composition of claim 2, wherein said compound is 4-benzyloxy-1-ethoxy-2,2,6,6-tetramethylpiperidine.

8. The composition of claim 2, wherein said compound is 1,4-di-(4-hydroxy-3,5-di-tert-butylbenzoyloxy)-2,2,6,6-tetramethylpiperidine.

9. The composition of claim 2, wherein said compound is alpha,alpha'-(di-1-benzyloxy-2,2,6,6-tetramethylpiperidin-4-yloxy)-p-xylene.

10. The composition of claim 2, wherein said compound is 4-benzoyloxy-1-(alpha-methylbenzyloxy)-2,2,6,6-tetramethylpiperidine.

11. The composition of claim 2, wherein said compound is di-[1-(alpha-methylbenzyloxy)-2,2,6,6-tetramethylpiperidin-4-yl]sebacate.

12. The composition of claim 2, wherein said compound is di-(1-cyclohexyloxy-2,2,6,6-tetramethylpiperidin-4-yl)sebacate.

13. The composition of claim 2, wherein said compound is di-(1-heptyloxy-2,2,6,6-tetramethylpiperidin-4-yl) sebacate.

14. The composition of claim 2, wherein said compound is di-(1-ethoxy-2,2,6,6-tetramethylpiperidin-4-yl)sebacate.

15. The composition of claim 2, wherein said compound is di-(1-nonyloxy-2,2,6,6-tetramethylpiperidin-4-yl)sebacate.

16. The composition of claim 2, wherein said compound is di-[1-(1-methylcyclohexyloxy)-2,2,6,6-tetramethylpiperidin-4-yl)sebacate.

17. The composition of claim 2, wherein said compound is di-(1-n-butylcarbamoyloxy-2,2,6,6-tetramethylpiperidin-4-yl)n-butylmalonate.

18. The composition of claim 2, wherein said compound is di-(1-octyloxy-2,2,6,6-tetramethylpiperidin-4-yl)sebacate.

19. The composition according to claim 1 wherein the compound of component (b) is contained in an amount of 0.1 to 10% by weight, based on resin solids.

20. The composition according to claim 1 which additionally contains (c) a UV absorber selected from the group consisting of benzophenones, benzotriazoles, acrylic acid derivatives, aryl-s-triazines, organic nickel compounds and oxanilides.

21. A composition according to claim 20 which contains a benzotriazole UV absorber selected from the group consisting of 2-[2-hydroxy-3,5-di(alpha,alpha-dimethylbenzyl)phenyl]-2H-benzotriazole, 2-(2-hydroxy-3,5-di-tert-octylphenyl)-2H-benzotriazole, 2-(2-hydroxy-3-alpha,alpha-dimethylbenzyl-5-tert-octylphenyl)-2H-benzotriazole, 2-(2-hydroxy-3-tert-octyl-5-alpha,alpha-dimethylbenzylphenyl)-2H-benzotriazole, 2-(2-hydroxy-5-tert-octylphenyl)-2-H-benzotriazole, 2-[2-hydroxy-3-tert-butyl-5-(2-(omega-hydroxy-octa(ethyleneoxy)carbonyl)-ethylphenyl)]-2H-benzotriazole, 2-(2-hydroxy-3,5-di-tert-amylphenyl)-2H-benzotriazole, dodecylated 2-(2-hydroxy-5-methylphenyl)-2H-benzotriazole, 5-chloro-2[2-hydroxy-3,5-di(alpha,alpha-dimethylbenzyl)-phenyl]-2H-benzotriazole, 5-chloro-2-(2-hydroxy-3,5-di-tert-octylphenyl)-2H-benzotriazole, 5-chloro-2-(2-hydroxy-3-alpha,alpha-dimethyl-tert-octylphenyl)-2H-benzotriazole, or 5-chloro-2-(2-hydroxy-3-tert-octyl-5-alpha,alpha-dimethylbenzylphenyl)-2H-benzotriazole, 5-chloro-2-[2-hydroxy-3-tert-butyl-5-(2-(omega-hydroxyocta(ethyleneoxy)-ethylphenyl]-2H-benzotriazole, 5-chloro-2-(2-hydroxy-5-tert-octylphenyl)-2H-benzotriazole, 5-chloro-2-(2-hydroxy-3,5-di-tert-amylphenyl)-2H-benzotriazole and 5-chloro-2-[2-hydroxy-3-tert.butyl-5-(2-octyloxycarbonyl)ethylphenyl]-2H-benzotriazole.

22. A composition according to claim 21, wherein the benzotriazole is 2-[2-hydroxy-3,5-di(alpha,alpha-dimethylbenzyl)phenyl]-2H-benzotriazole, 2-[2-hydroxy-3-tert-butyl-5-(2-(omega-hydroxy-octa-(ethyleneoxy)carbonyl)ethylphenyl]-2H-benzotriazole, 2-[2-hydroxy-3-tert.butyl-5-(2octyloxycarbonyl)ethylphenyl]-2H-benzotriazole or 5-chloro2-[2-hydroxy-3-tert.butyl-5-(2-octyloxycarbonyl)ethylphenyl]-2H-benzotriazole.

23. The composition according to claim 20, wherein the total amount of component (b) plus component (c) is 0.2 to 20% by weight based on resin solids.

24. The composition according to claim 20 which additionally contains a phosphite or phosphonite antioxidant.

25. The composition according to claim 24 which additionally contains a hindered phenol antioxidant.

26. The composition according to claim 1 wherein said resin is selected from the group consisting of unmodified alkyd, acrylic, acrylic alkyd or polyester resins; said resins modified with silicon, isocyanates, isocyanurates, ketimines or oxazolidines; crosslinked epoxy resins; and epoxy-crosslinked acrylic and polyester resins.

27. The composition according to claim 1, which is an enamel for industrial finishes.

28. The composition according to claim 1 which is a finishing enamel for automobiles.

* * * * *